(12) United States Patent
Patkar et al.

(10) Patent No.: US 12,011,356 B2
(45) Date of Patent: Jun. 18, 2024

(54) HUMERAL HEAD AND CUP TRIAL WITH FLEXURE

(71) Applicant: Howmedica Osteonics Corp., Mahwah, NJ (US)

(72) Inventors: Pranoti Patkar, Mumbai (IN); Ashish Mehta, Rajasthan (IN); Sunny Shorabh, Ghaziabad (IN); Rakesh Kumar, Daltonganj (IN); Rajan Yadav, New Delhi (IN); Shashank Verma, Agra (IN)

(73) Assignee: Howmedica Osteonics Corp., Mahwah, NJ (US)

( * ) Notice: Subject to any disclaimer, the term of this patent is extended or adjusted under 35 U.S.C. 154(b) by 520 days.

(21) Appl. No.: 17/322,110

(22) Filed: May 17, 2021

(65) Prior Publication Data

US 2022/0362030 A1 Nov. 17, 2022

(51) Int. Cl.
*A61F 2/40* (2006.01)
*A61F 2/46* (2006.01)

(52) U.S. Cl.
CPC .......... *A61F 2/4014* (2013.01); *A61F 2/4612* (2013.01); *A61F 2/4684* (2013.01); *A61F 2002/4022* (2013.01)

(58) Field of Classification Search
CPC .... A61F 2/4014; A61F 2/4612; A61F 2/4684; A61F 2002/4022; A61F 2/4059; A61F 2002/30332; A61F 2002/305; A61F 2002/30505; A61F 2002/30565; A61F 2002/4037; A61F 2002/4044; A61B 17/1684
See application file for complete search history.

(56) References Cited

U.S. PATENT DOCUMENTS

| 6,673,114 B2 | 1/2004 | Hartdegen et al. |
| 6,776,799 B2 | 8/2004 | Ball et al. |
| 7,431,736 B2 | 10/2008 | Maroney et al. |
| 7,632,283 B2 | 12/2009 | Heldreth |
| 8,663,334 B2 | 3/2014 | Viscardi et al. |
| 8,753,402 B2 | 6/2014 | Winslow et al. |
| 8,858,641 B2 | 10/2014 | Viscardi et al. |
| 8,906,102 B2 | 12/2014 | Viscardi et al. |

(Continued)

FOREIGN PATENT DOCUMENTS

| CA | 2347042 A1 | 3/2001 |
| EP | 2668930 A1 | 12/2013 |

OTHER PUBLICATIONS

Kolken et al., Auxetic mechanical metamaterials, RSC Advances, Jan. 2017, pp. 5111-5129, The Royal Society of Chemistry.

*Primary Examiner* — Sarah W Aleman
*Assistant Examiner* — Mikail A Mannan
(74) *Attorney, Agent, or Firm* — Lerner David LLP

(57) ABSTRACT

Disclosed herein is a humeral head and cup trials, a system for humeral trialing, and a method for removing a humeral head and cup trial from a humeral stem. The humeral trial may include a first portion, a second portion, and a post extending from the second portion. The first portion may define an articular surface. The post may define a first length in a first configuration and a second length in a second configuration. The first length may be greater than the second length. The post may change from the first configuration to the second configuration by moving the first portion with respect to the second portion.

12 Claims, 21 Drawing Sheets

(56) References Cited

U.S. PATENT DOCUMENTS

| | | |
|---|---|---|
| 8,945,138 B2 | 2/2015 | Klotz et al. |
| 9,216,090 B2 | 12/2015 | Metcalfe |
| 9,510,952 B2 | 12/2016 | Muir et al. |
| 9,597,191 B2 | 3/2017 | Muir et al. |
| 9,681,954 B2 | 6/2017 | Klotz |
| 10,034,759 B2 | 7/2018 | Deransart et al. |
| 10,245,164 B2 | 4/2019 | Muir et al. |
| 10,390,972 B2 | 8/2019 | Rao |
| 10,588,752 B2 | 3/2020 | Winslow et al. |
| 2008/0161823 A1* | 7/2008 | Klotz .................... A61F 2/4684 606/102 |
| 2017/0281355 A1 | 10/2017 | Winslow et al. |
| 2018/0133018 A1 | 5/2018 | Winslow |
| 2018/0168815 A1 | 6/2018 | Muir et al. |

* cited by examiner

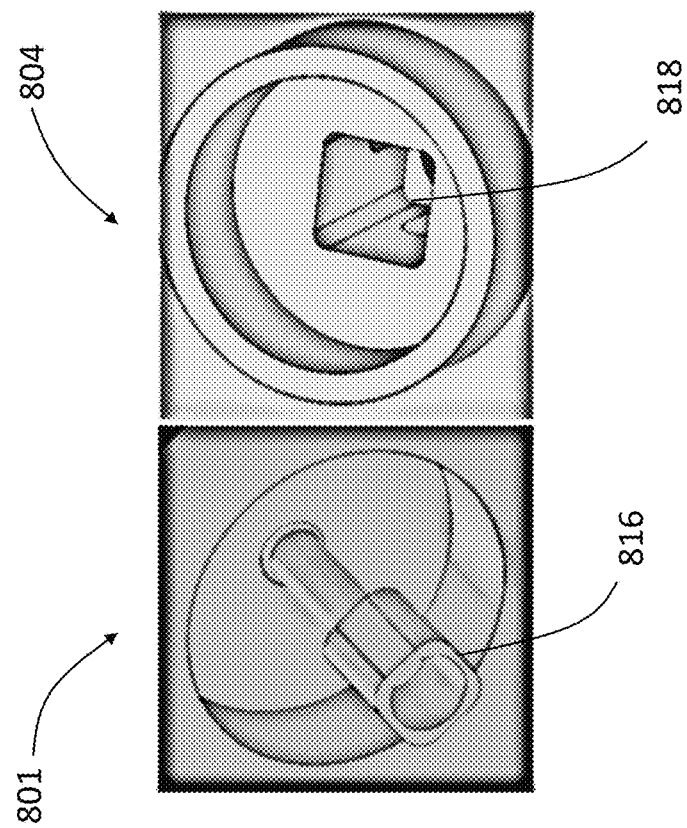
FIG. 25
FIG. 26
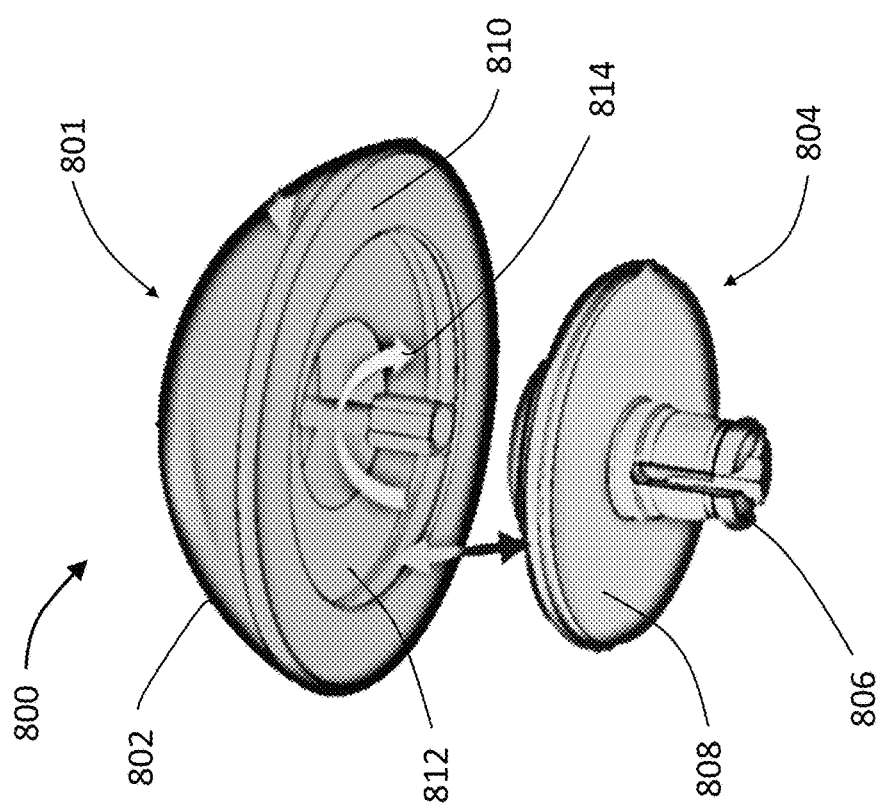
FIG. 24

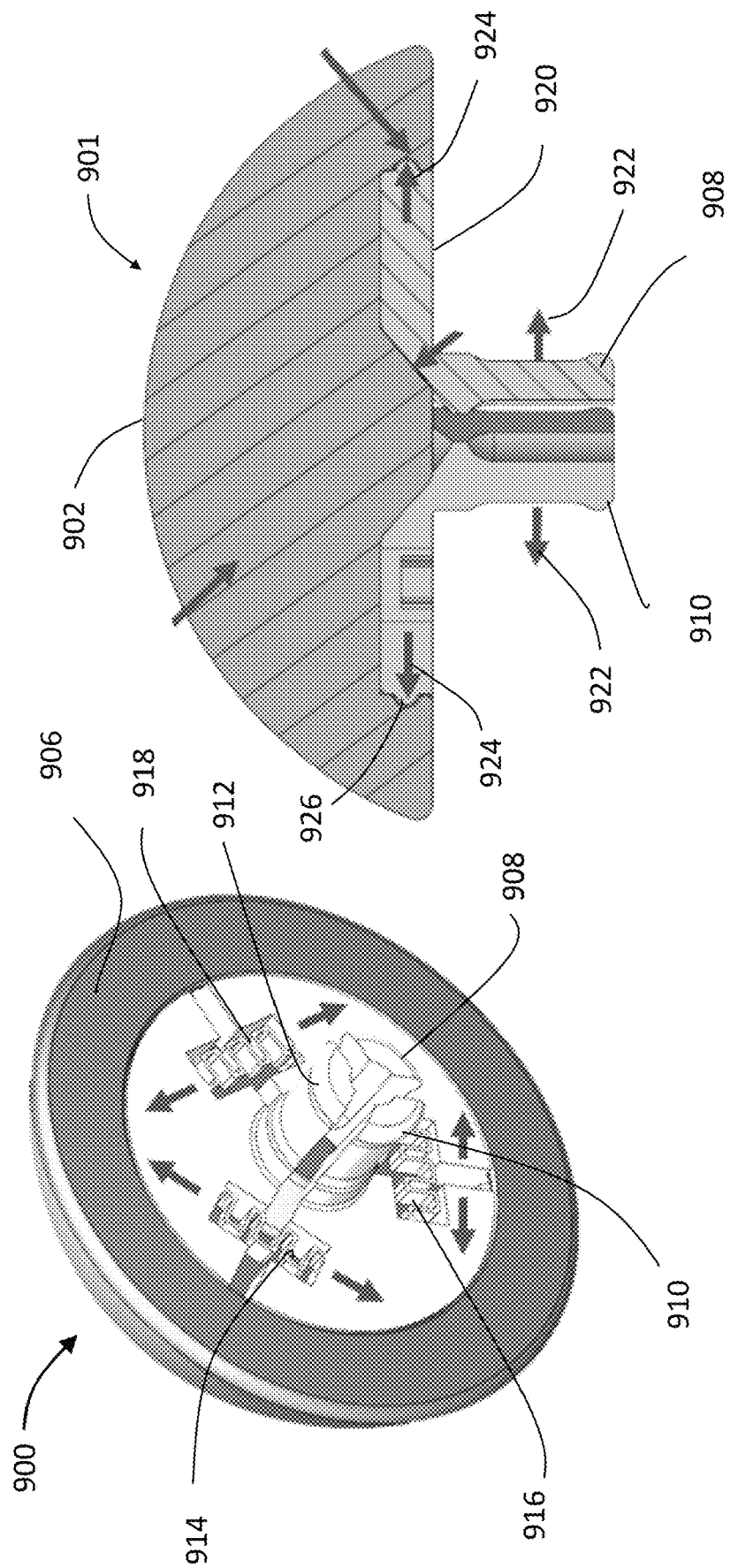

HUMERAL HEAD AND CUP TRIAL WITH FLEXURE

FIELD OF THE DISCLOSURE

The present disclosure relates generally to an apparatus and a method of sizing implants, and in particular relates to a trial and a method for using a trial for implant sizing.

BACKGROUND OF THE DISCLOSURE

In an orthopedic joint replacement procedure, a surgeon may use a trial that is representative of a prosthesis or implant to assess the size and placement of the prosthesis or implant prior to implantation. In some instances, the trial preferably is secured firmly on an implant or a second trial to allow for articulation of a patient's joint with the trial secured to the implant in order to evaluate the trial, and thus the prosthesis or implant represented by the trial. However, firmly securing a trial to the implant may prevent ready attachment and detachment of the trial to and from the implant. Further, removing a firmly secured trial from an implant may require significant extraction forces which may be transferred to the implant during removal.

Various extractors may be used for pulling, manipulating and/or inserting the trial of an implant into the implant site. Such extractors may also be used for removing a trial of an implant, or the implant itself, from cemented or cementless applications. In such solutions there is a risk of damaging the bone periphery, the soft tissues and the bone implant site. The connection between the extractor and the implant in many such systems may be achieved through cumbersome and time consuming means that do not effectively and easily engage the extractor and quickly remove the implant. For example, many extractors are threaded directly onto the trial.

Thus, an improved trial and a method for implant sizing using a trial are desired.

BRIEF SUMMARY OF THE DISCLOSURE

In certain embodiments, the present disclosure relates generally to a humeral head and cup trials. In other embodiments, the present disclosure relates to a system for humeral trialing. In still other embodiments, the present disclosure relates to a method for removing a humeral head and cup trials from a humeral stem.

In an aspect of the present disclosure, a humeral trial is provided. In accordance with this aspect, the humeral trial may include a first portion defining a convex articular surface, a second portion defining a flat surface, and a post extending from the second portion. The post may have a first leg and a second leg in contact with a flexure member. The post may define a first length in a first configuration and a second length in a second configuration. The first length may be greater than the second length. The post may be configured to transition from the first configuration to the second configuration upon movement of the first portion with respect to the second portion.

Continuing in accordance with this aspect, the humeral trial may be adapted to be secured to a prosthetic humeral stem when the post is in an opening of the prosthetic humeral stem in the first configuration. The first length may be equal to or larger than an opening length of the opening such that the post may form an interference fit with the opening in the first configuration. The humeral trial may be adapted to be detached from the humeral stem by removing the post from the opening in the second configuration. The second length may be smaller than the opening length such that the post may be removed from the opening in the second configuration. The post may be adapted to be removed from the opening in the second configuration without contacting sidewalls of the opening. The first portion may be adapted to articulate with a glenoid, a glenoid implant, or a glenoid trial through a range of shoulder motion when the humeral trial is secured to the humeral stem.

Continuing in accordance with this aspect, the flexure member may be disposed between the first and second legs. The flexure member may push the first leg and second legs away from each other when subjected to a first force. The first force may act in a direction from the first portion toward the second portion. The flexure member may pull together the first and second legs toward each other when subjected to a second force. The second force may act in a direction from the second portion toward the first portion.

Continuing in accordance with this aspect, the humeral trial may be a humeral head trial.

In another aspect of the present disclosure, a humeral trial is provided. The humeral trial according to this aspect may include a first portion defining a concave articular surface, a second portion defining a flat surface and a post extending from the second portion. The first portion may be detachably coupled with the second portion. The post may have a first leg and a second leg in contact with a flexure member. The post may define a first length in a first configuration and a second length in a second configuration. The first length may be greater than the second length. The post may be configured to transition from the first configuration to the second configuration upon movement of the first portion with respect to the second portion.

In another aspect of the present disclosure, a trial kit is provided. A trial kit according to this aspect may include a humeral trial and a tool. The humeral trial may have a first portion defining an articular surface, a second portion defining a flat surface, and a post extending from the second portion. The post may have a first leg and a second leg in contact with a flexure member. The post may define a first length in a first configuration and a second length in a second configuration. The first length may be greater than the second length. The tool may be used for attaching and removing the humeral trial to a humeral stem. The tool may include first and second arms. The first arm may contact the first leg to move the post from the first configuration to a second configuration.

Continuing in accordance with this aspect, the humeral trial may be a humeral head trial and the articular surface may be a convex articular surface.

Continuing in accordance with this aspect, the humeral trial may be a humeral cup trial and the articular surface may be a concave articular surface. The first portion may be configured to be detachably coupled with the second portion.

Continuing in accordance with this aspect, the humeral trial may be adapted to be secured to the humeral stem when the post is in an opening of the prosthetic humeral stem in the first configuration. The first length may be equal to or larger than an opening length of the opening such that the post forms an interference fit with the opening in the first configuration.

Continuing in accordance with this aspect, the humeral trial may be adapted to be detached from the humeral stem by removing the post from the opening in the second configuration. The second length may be smaller than the opening length such that the post may be removed from the opening in the second configuration. The post may be adapted to be removed from the opening in the second configuration without contacting sidewalls of the opening.

Continuing in accordance with this aspect, the first portion may be adapted to articulate with a glenoid, a glenoid implant, or a glenoid trial through a range of shoulder motion when the humeral trial is secured to the humeral stem.

Continuing in accordance with this aspect, the second arm may contact the second leg to move the post from the first configuration to a second configuration. The first arm may be connected to a first lever and the second arm may be connected to a second lever. The first and second arms may form a hinged joint.

Continuing in accordance with this aspect, the first arm may be received in a first groove on the second portion. The second arm may be received in a second groove on the second portion.

BRIEF DESCRIPTION OF THE DRAWINGS

A more complete appreciation of the subject matter of the present disclosure and the various advantages thereof may be realized by reference to the following detailed description, in which reference is made to the following accompanying drawings:

FIG. 24 is an exploded view of a humeral head trial assembly according to another embodiment of the present disclosure;

FIG. 25 is a partial bottom view of a humeral head trial of FIG. 24;

FIG. 26 is a partial top view of a collet base of the humeral head trial assembly of FIG. 24;

FIG. 30 is bottom perspective view of the humeral head trial assembly of FIG. 29;

FIG. 31 is side cross-sectional view of the humeral head trial assembly of FIG. 29;

DETAILED DESCRIPTION

Reference will now be made in detail to the various embodiments of the present disclosure illustrated in the accompanying drawings. Wherever possible, the same or like reference numbers will be used throughout the drawings to refer to the same or like features. It should be noted that the drawings are in simplified form and are not drawn to precise scale. Additionally, the term "a," as used in the specification, means "at least one." The terminology includes the words above specifically mentioned, derivatives thereof, and words of similar import. Although at least two variations are described herein, other variations may include aspects described herein combined in any suitable manner having combinations of all or some of the aspects described. As used herein, the terms "implant trial" and "trial" will be used interchangeably and as such, unless otherwise stated, the explicit use of either term is inclusive of the other term. Similarly, the terms "implant" and "prosthesis" will be used interchangeably and as such, unless otherwise stated, the explicit use of either term is inclusive of the other term.

In describing preferred embodiments of the disclosure, reference will be made to directional nomenclature used in describing the human body. It is noted that this nomenclature is used only for convenience and that it is not intended to be limiting with respect to the scope of the invention. For example, as used herein, the term "distal" means toward the human body and/or away from the operator, and the term "proximal" means away from the human body and/or towards the operator.

Figure 2:
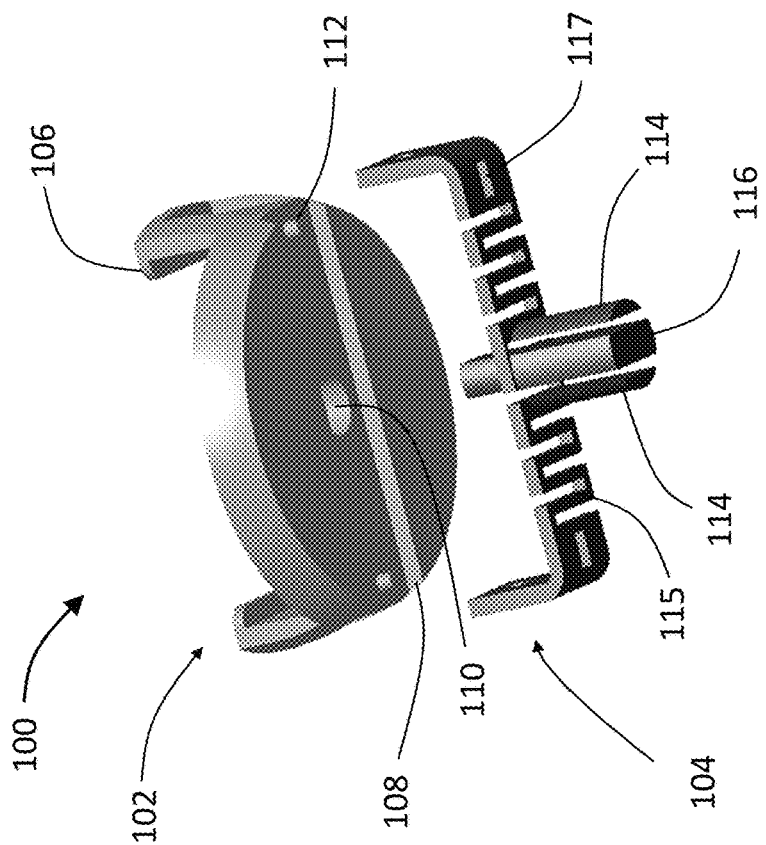
FIG. 2 is an exploded view of the humeral cup trial insert assembly of FIG. 1.
Figure 1:
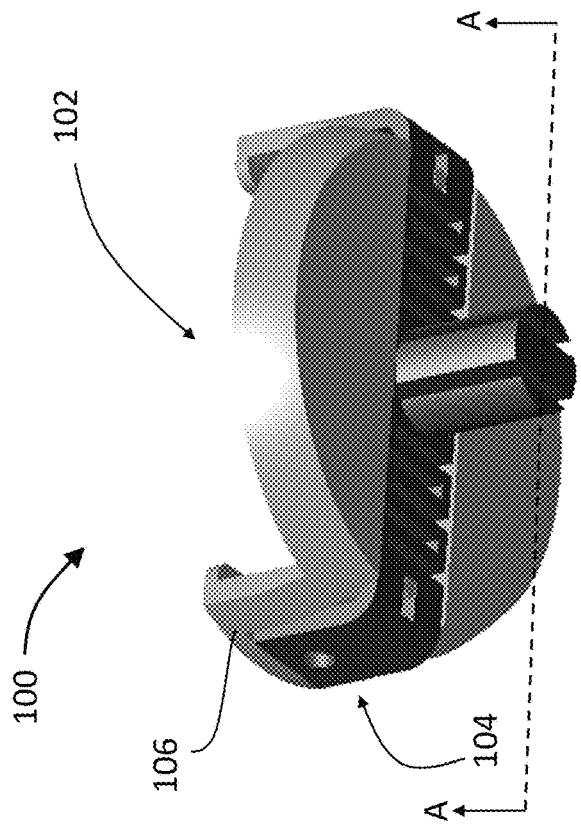
FIG. 1 is a front perspective view of a humeral cup trial insert assembly according to an embodiment of the present disclosure.
Figure 4:
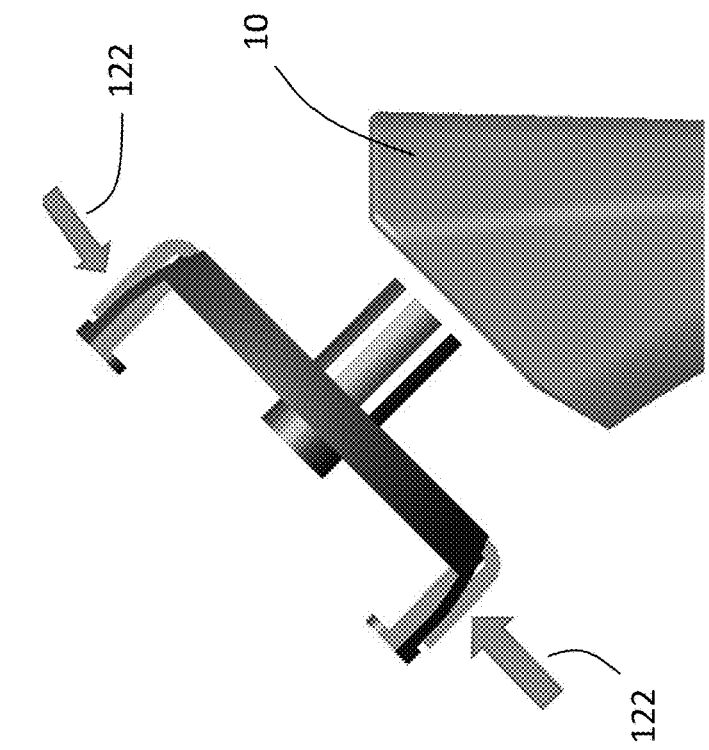
FIG. 4 is a side view of the humeral cup trial insert assembly of FIG. 1 and an implant.
Figure 3:
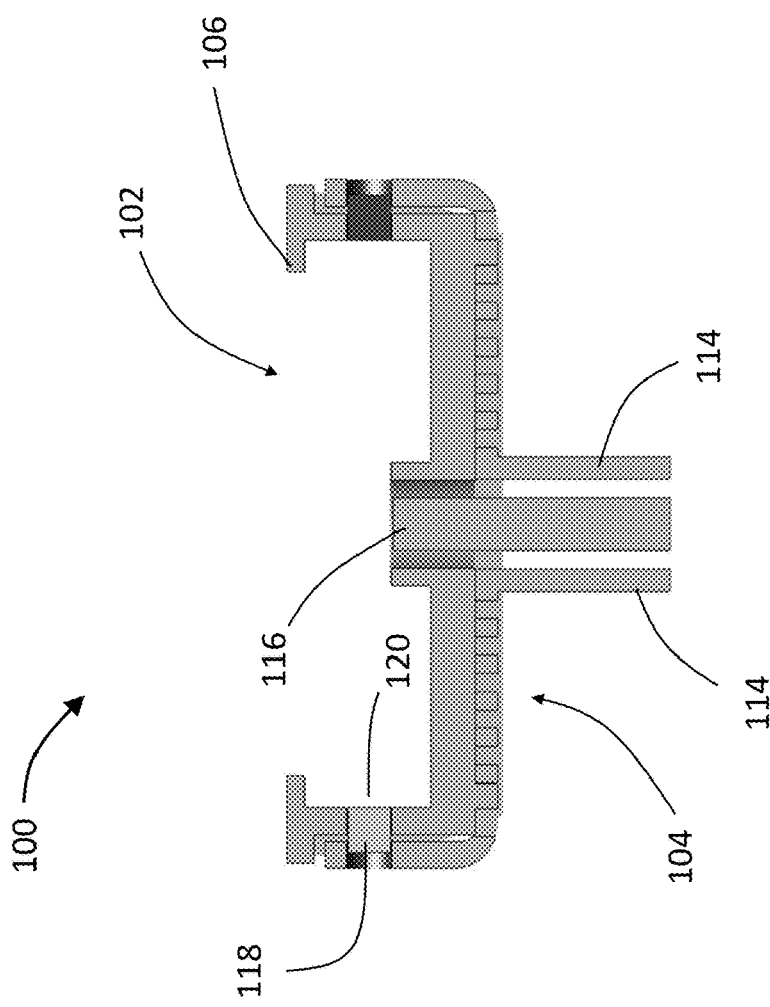
FIG. 3 is a cross-sectional view of the humeral cup trial insert assembly of FIG. 1 taken along line A-A.

Referring now to FIGS. 1-4, there is shown a humeral cup trial insert assembly 100 according to an embodiment of the present disclosure. Humeral cup trial insert assembly 100 includes an insert 102 and a flexure 104. Flexure 104 includes legs 114 connected to flexible members 115 as best shown in FIGS. 2 and 3. Flexible members 115 may include generally "U"-shaped (or other zig-zag) members that are positioned continuously in series, such that the flexible members 115 include lateral walls that are interrupted by recesses or gaps, with the lateral walls connected via transverse members. With this configuration, compressing the flexible members toward each other will tend to reduce the size of the recesses or gaps in the lateral walls, and bring legs 114 closer to post 116. Flexure 104 can be detachably attached to insert 102 by flexing and placing tabs 118 of flexure 104 in corresponding recesses 120 of insert 102 as best shown in FIG. 3. In another embodiment, insert 102 can include tabs that can be placed in corresponding recesses in flexure 104. A groove 108 extending across a distal surface of insert 102 is configured to receive flexure 104 as shown in FIG. 2. A post 116 extending proximally from flexure 104 is received in a recess 110 in groove 108 to secure flexure 104 to insert 102. Compressing flexure 104 by applying force along direction arrows 122 moves legs 114 toward post 116, and allows insertion of the legs 114 and post 116 into a corresponding tapered recess of an implant 10. Once the applied force is removed, the flexible members 115 will try to return to their non-compressed state, causing legs 114 to expand away from post 116. The tendency for the legs 114 to move away from the post 116 will cause friction on the surface defining the corresponding recess in implant 10, so that the humeral cup trial insert assembly 100 is firmly attached to implant 10. Insert 102 includes pins 112 extending away from the insert as best shown in FIG. 2. Pins 112 are configured to be received in corresponding slots 117 of flexure 104. Slots 117 function as tracks for pins 112 to allow movement of the pins within these slots during compression and expansion of flexure 104. After trialing is performed, an operator can readily remove humeral cup trial insert assembly 100 by applying force along direction arrows 122 to move legs 114 closer to post 116 in order to release humeral cup trial insert assembly 100. Thus, humeral cup trial insert assembly 100 can be readily inserted and removed from implant 10 with minimal pull-out force on the implant. Further, flexure 104 ensures that humeral cup trial insert is securely attached to implant 10 to allow a surgeon to perform various trialing related activity without disturbing the humeral head trial position on the implant. Overhangs 106 on insert 102 (FIG. 2) are provided to secure a slidable humeral cup trial or implant to the humeral cup trial assembly. It should be understood that the implant 10 shown in FIG. 4 may be a prosthetic humeral stem, and the implant 10 may be implanted into a patient's proximal humerus during trialing. After the humeral cup trial insert assembly 100 is coupled to humeral stem 10, a humeral cup implant or humeral cup trial (not illustrated) may be coupled to the insert 102. With the humeral cup implant or humeral cup trial coupled to insert 102, trialing of the humeral cup trial may be performed against a glenosphere implant or glenosphere trial (not illustrated) that is coupled to the patient's glenoid, the trialing allowing for evaluation of a reverse shoulder arthroplasty ("RSA") system. It may be desirable to minimize pull-out force of the humeral cup trial insert assembly 100 from the implant 10 to minimize the chance of unintentionally changing the position of the implant 10 within the patient's humerus while attempting to remove the humeral cup trial assembly 100 after trialing is complete. Although flexure 104 is illustrated with two flexible members 115 (and two corresponding legs 114), in other embodiments the flexure 104 may include only a single flexible member 115 (and one corresponding moveable leg 114), with the opposite side being fixed or non-flexible. Further, it should be understood that a humeral head trial (similar to that shown in FIG. 9) may instead by used with the flexure 104 for use in trialing during a total (i.e. standard, non-reverse) shoulder arthroplasty ("TSA") procedure. In such an embodiment, the humeral head trial includes features to couple to the flexure 104 similar to those described in connection with humeral cup trial insert 102.

Figure 6:
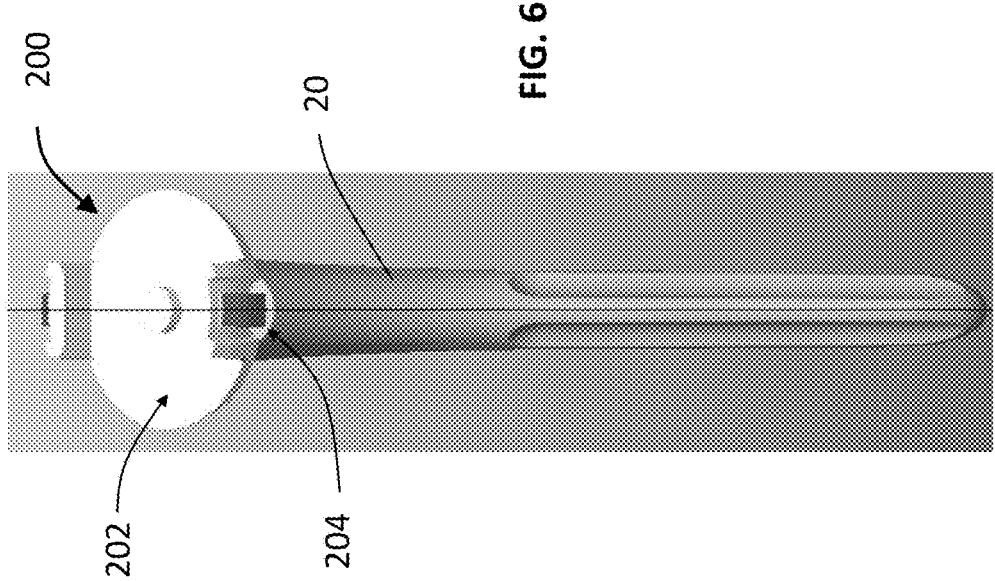
FIG. 6 is a side view of the humeral cup trial insert assembly of FIG. 5 coupled to an implant.
Figure 5:
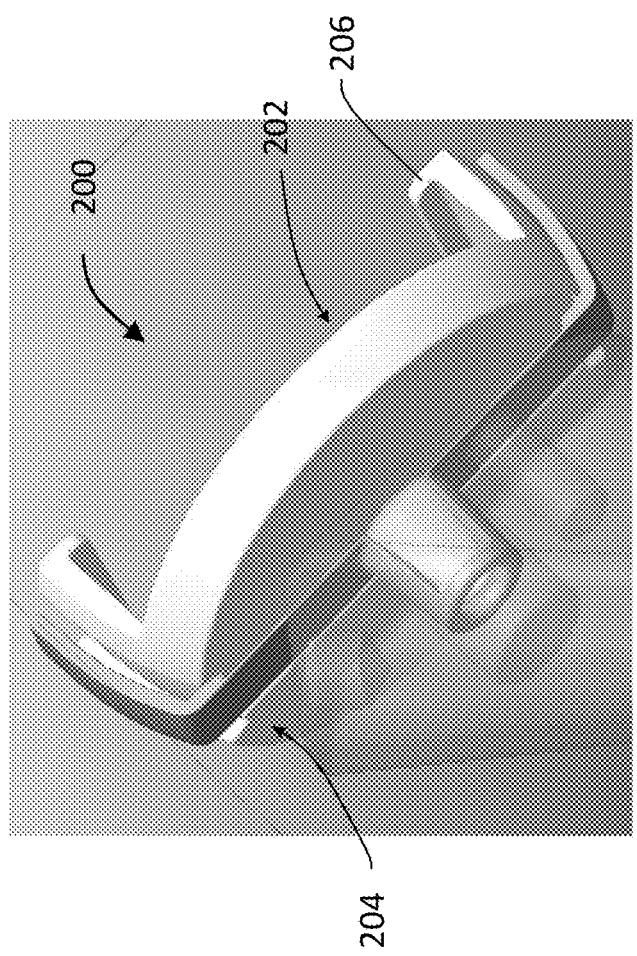
FIG. 5 is a side perspective view of a humeral cup trial insert assembly according to another embodiment of the present disclosure.
Figures 7, 8:
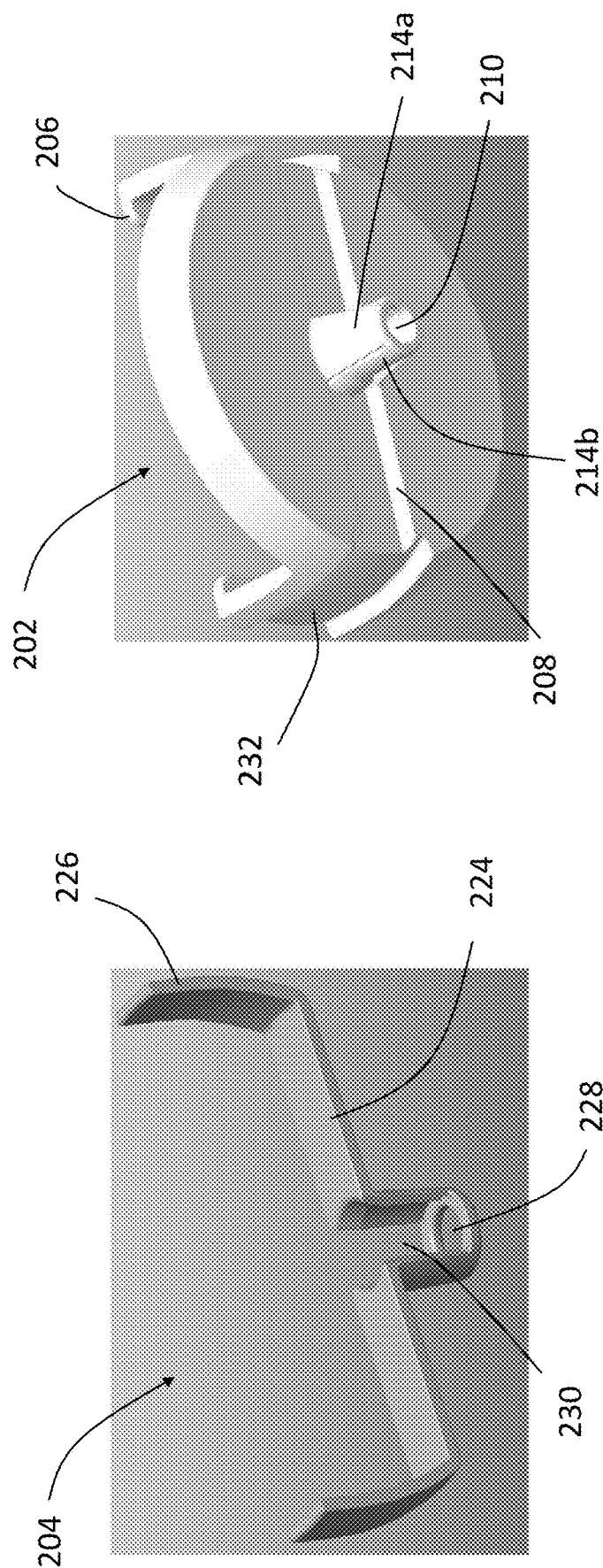
FIG. 7 is a top perspective view of a sleeve of the humeral cup trial insert assembly of FIG. 5.
FIG. 8 is a bottom perspective view of an insert of the humeral cup trial insert assembly of FIG. 5.

FIGS. 5-8 show a humeral cup trial insert assembly 200 according to another embodiment of the present disclosure. Humeral cup trial insert assembly 200 includes an insert 202 and an attachable sleeve 204. Sleeve 204 may be formed of plastic or another suitable material, and may include two legs 224 extending opposite a central protrusion 230 (which may have a conical/tapered shape), and two arms 226. Each arm 226 may extend upwardly from the end of a corresponding leg 224 in a direction away from the central protrusion 230, and each arm 226 may have a slight curvature. The insert 202 may include a number of complementary features to the sleeve 204. For example, the bottom surface of the insert 202 may include a bottom groove 208 sized and shaped to receive the two legs 224 of the sleeve 204, and two side grooves 232 sized and shaped to receive the two arms 226 of the sleeve 204 therein. The central protrusion 230 of the sleeve 204 may include an opening 228, and two side walls connecting the central protrusion to the legs 224. The side walls of the central protrusion of the sleeve 204 may be non-continuous so that gaps are formed circumferentially between the side walls. The insert 202 may include a central protrusion that is generally complementary in shape and size (e.g. tapered/conical shape) to the central protrusion of the sleeve 204, the central protrusion of the insert 202 adapted to be received within the central protrusion of the sleeve 204. The central protrusion of the insert 202 may include two fixed sidewalls 214a on diametrically opposed sides of the central protrusion, and two flexure sidewalls 214b positioned circumferentially between the fixed sidewalls. The central protrusion of the insert 202 may define an opening 210, and the two fixed sidewalls 214a may be fixedly coupled to the bottom surface of the insert 202. However, the two flexure sidewalls 214b may not be directly fixed to either the bottom surface of the insert 202 or to the fixed sidewalls 214a except for the portions adjacent the opening 210. With this configuration, the two flexure sidewalls 214b may be pressed radially inwardly and thus flex inwardly to temporarily decrease one of the diameter dimensions of the central protrusion. In use, the central protrusion of the sleeve 204 may first be inserted into a corresponding tapered/conical recess in implant 20, which may be a humeral stem implant substantially similar to implant 10. The central protrusion 230 of the sleeve 204, including the sidewalls thereof, will tend to have an interference fit to keep the sleeve 204 fixed to the implant 20. Then, the central protrusion of the insert 202 may be inserted into the central protrusion 230 of the sleeve 204, with the flexure sidewalls 214b in contact with the sidewalls of the central protrusion of the sleeve 204, and the fixed sidewalls 214a positioned within the gaps of the central protrusion of the sleeve 204 (as best shown in FIG. 6). With the humeral cup trial insert assembly 200 coupled to the implant 20, a humeral cup implant or humeral cup trial may be coupled to the insert 202 for trialing in an RSA implant procedure similar to the procedure described above in connection with FIGS. 1-4. Overhangs 206 on insert 202 (FIG. 8) are provided to secure a slidable humeral cup trial or implant to the humeral cup trial assembly. In order to release the humeral cup trial insert assembly 200 from the implant 20 with minimal pull-out force, the user may simply compress the arms 226 inwardly, causing the sidewalls of the central protrusion of the sleeve to press inwardly against the flexure sidewalls 214b. Because the flexure sidewalls 214b are capable of flexing, they will also move radially inward when the arms 226 are compressed inwardly. Thus, the interference fit of the central protrusion of the sleeve 204 with the implant 20 will relax upon compressing the arms 226 inwardly, allowing the humeral cup trial insert assembly 200 to be removed from the implant 20 with minimal pull-out force. It should further be understood that the sleeve 204 may instead be used with a humeral head trial having similar flexure features as insert 202 to provide for trialing of a humeral head in a TSA system.

Figure 9:
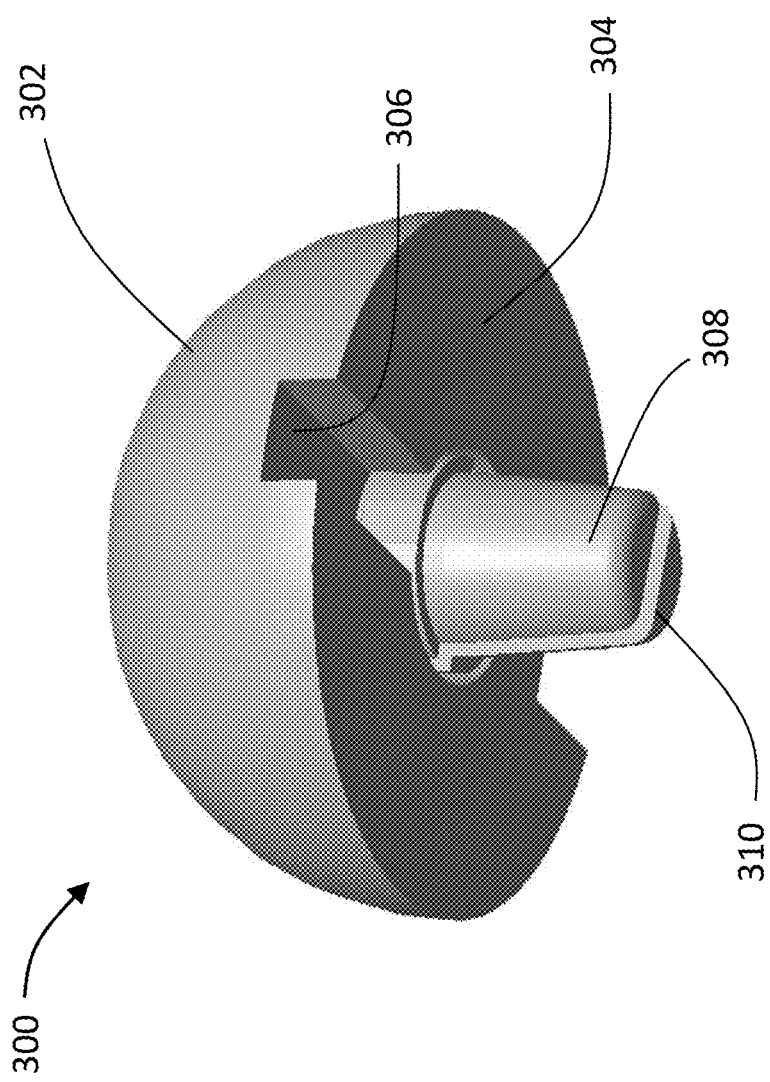
FIG. 9 is a side perspective view of humeral head trial according to an embodiment of the present disclosure.
Figure 11:
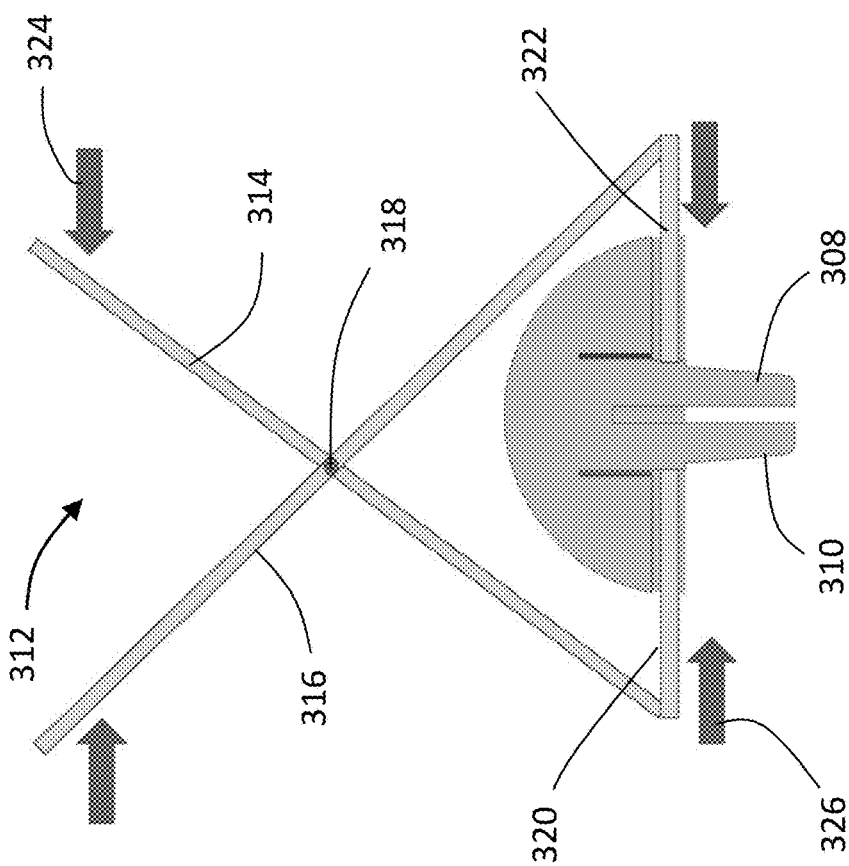
FIG. 11 is a side cross-sectional view of the humeral head trial of FIG. 9 in conjunction with a trial removal tool.
Figure 10:
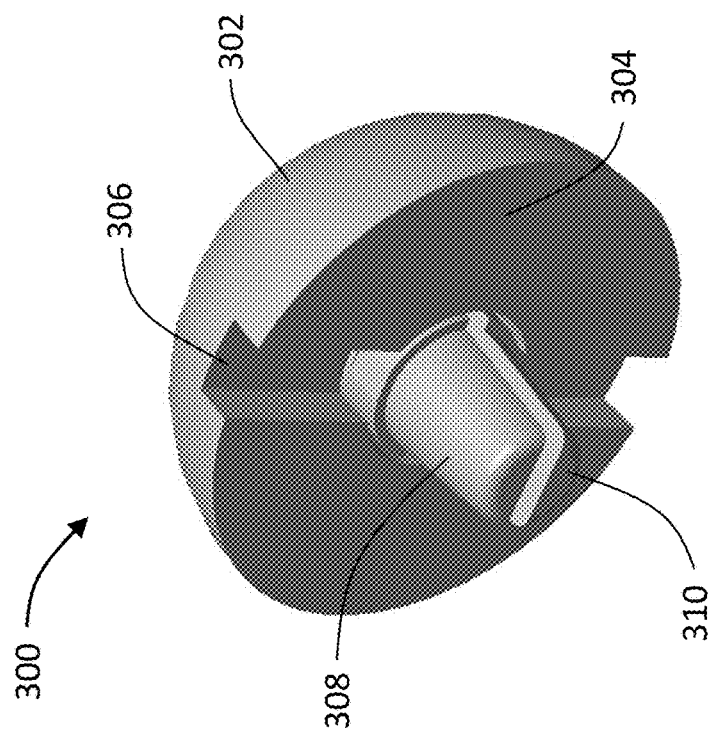
FIG. 10 is a bottom perspective view of the humeral head trial of FIG. 9.

Referring now to FIGS. 9 and 10 there is a shown a humeral head trial 300 according to an embodiment of the present disclosure. Humeral head trial 300 has a convex articular surface 302 and a flat surface 304. Articular surface 302 is configured to articulate with a glenoid, a glenoid implant or a glenoid trial through a range of shoulder motion when humeral head trial 300 is attached to a prosthetic humeral stem or base. A generally conical and/or tapered post having a first leg 308 and a second leg 310 extends from flat surface 304, the first and second legs 308, 310 having a gap or recess space between them. The first leg 308 and second leg 310 may be thought of as flexure legs, as the space between them allow the legs 308, 310 to move toward one another when compressed. A groove 306 that extends from the flat surface 304 a distance into the articular surface 302 provides side openings that allows access by a trial removal tool 312 to manipulate first and second legs 308, 310 as shown in FIG. 11.

In use, the tapered post of the humeral head trial 300 may be inserted into a corresponding conical or tapered recess in an prosthetic humeral stem or base, for example such as implant 10 or implant 20. The first and second legs 308, 310 may provide for an interference fit with the corresponding recess of the humeral implant to maintain the humeral head trial 300 secured to the implant for trialing. After trialing, the humeral head trial 300 may be removed from the humeral stem implant or base with minimal pull-out force by using the trial removal tool 312. Referring to FIG. 11, the trial removal tool 312 may include levers 314 and 316 at proximal free ends of the tool 312, the levers 314, 316 being attached to each other at a hinge 318. The trial implant removal tool 312 may include two arms 320, 322 at distal free ends of the tool 312. In the illustrated embodiment, arm 320 is integral with lever 314, and arm 322 is integral with lever 316. In order to remove the humeral head trial 300 from the implant, the arms 320, 322 may be passed through the openings defined by groove 306 until the terminal ends of the arms 320, 322 contact or are positioned adjacent the legs 308, 310 of the post of the humeral head trial 300. Force applied at the proximal ends of levers 314 and 316 as shown by direction arrows 324 results in arms 320 and 322 pushing first leg 308 and second leg 310 toward each other, causing the gap space between the first and second legs 308, 310 to reduce, allowing for removal of the humeral head trial 300 from the humeral stem implant or base without placing any significant pull-out force on the humeral stem implant or base.

Figure 12:
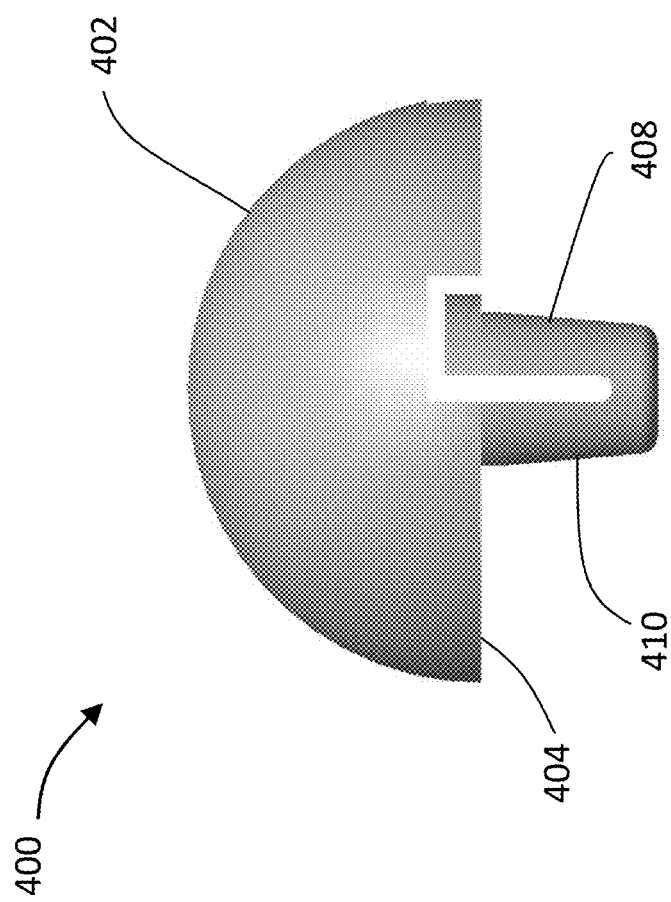
FIG. 12 is a side view of a humeral head trial according to another embodiment of the present disclosure.
Figure 14:
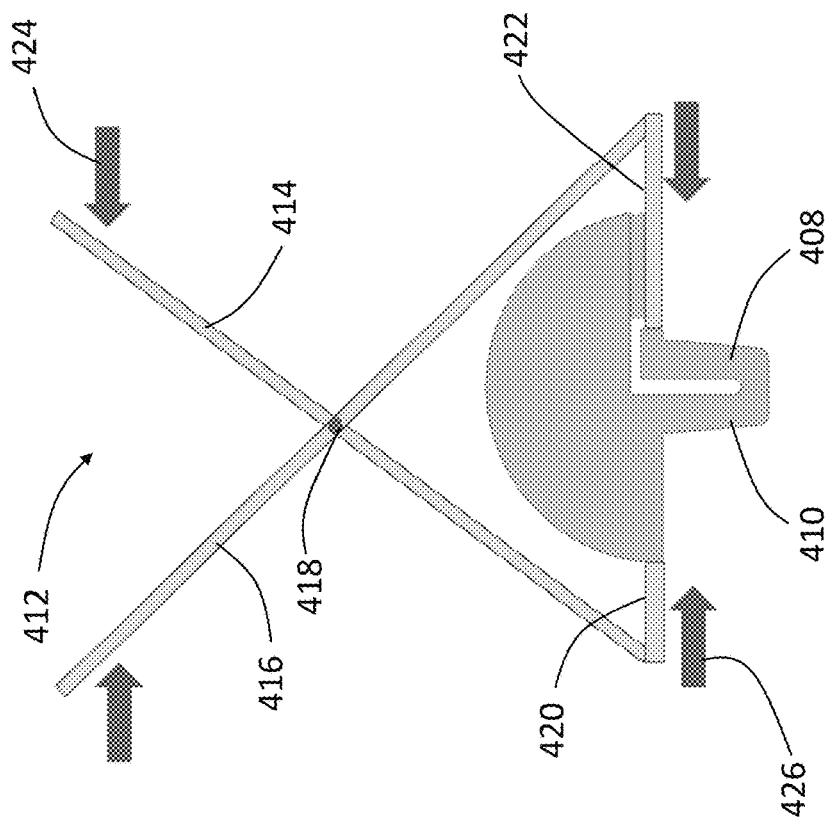
FIG. 14 is a side cross-sectional view of the humeral head trial of FIG. 12 in conjunction with a trial removal tool.
Figure 13:
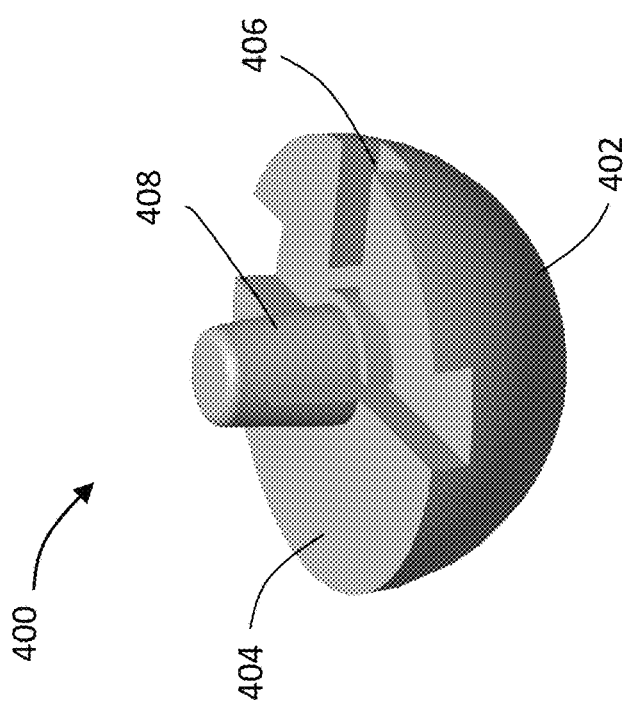
FIG. 13 is a bottom perspective view of the humeral head trial of FIG. 13.

FIGS. 12-14 show a humeral head trial 400 according to another embodiment of the present disclosure. Humeral head trial 400 is similar to humeral head trial 300 and therefore like elements are referred to with similar numerals within the 400-series. For instance, humeral head trial 400 includes articular surface 402, flat surface 404, and groove 406. However, only first leg 408 is movable in humeral head trial 400 as shown in FIG. 14. This may be achieved, for example, by having the bottom of legs 408, 410 fixedly coupled to one another, while only the top of leg 410 is fixedly coupled to the flat surface 404. The top of leg 408 may remain a spaced distance from the flat surface 404 within groove 406, with a gap defined between legs 408 and 410. Trial removal tool 412 is similar to tool 312 and therefore like elements are referred to with similar numerals within the 400-series. For example, trial removal tool 412 includes levers 414 and 416 connected to arms 420 and 422. However, arm 420 is used to grip humeral head trial 400 and arm 422 moves first leg 408 as best shown in FIG. 14. Otherwise, the use of humeral head trial 400 is similar or identical to that described in connection with humeral head trial 300, and the use of trial removal tool 412 is similar or identical to that described in conjunction with trial removal tool 412.

Figure 15:
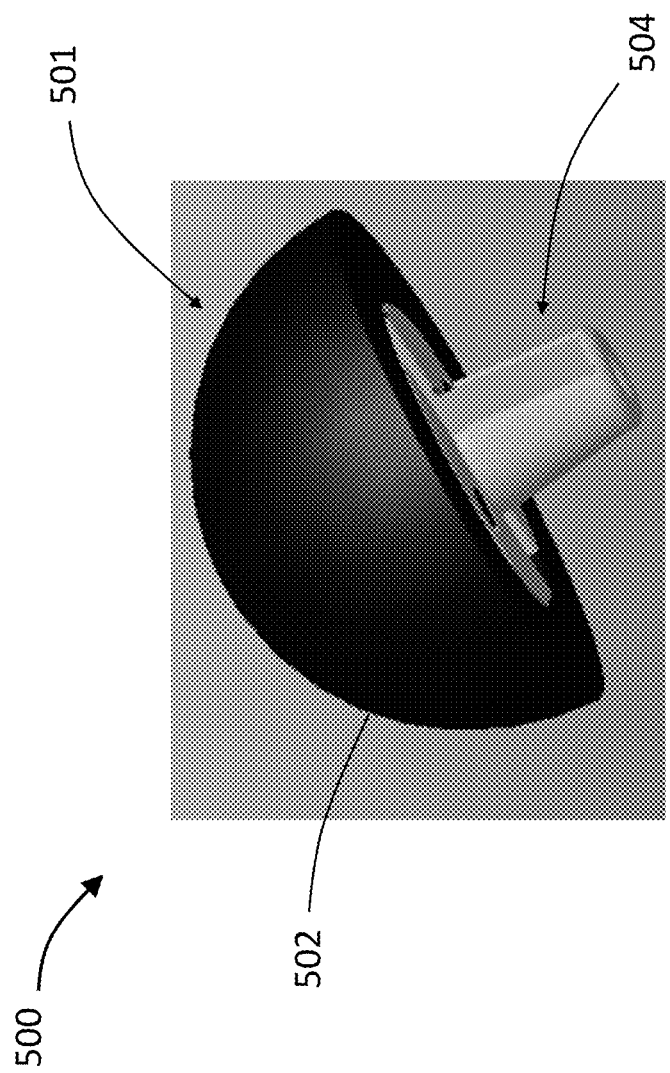
FIG. 15 is a side perspective view of a humeral head trial assembly according to another embodiment of the present disclosure.
Figure 17:
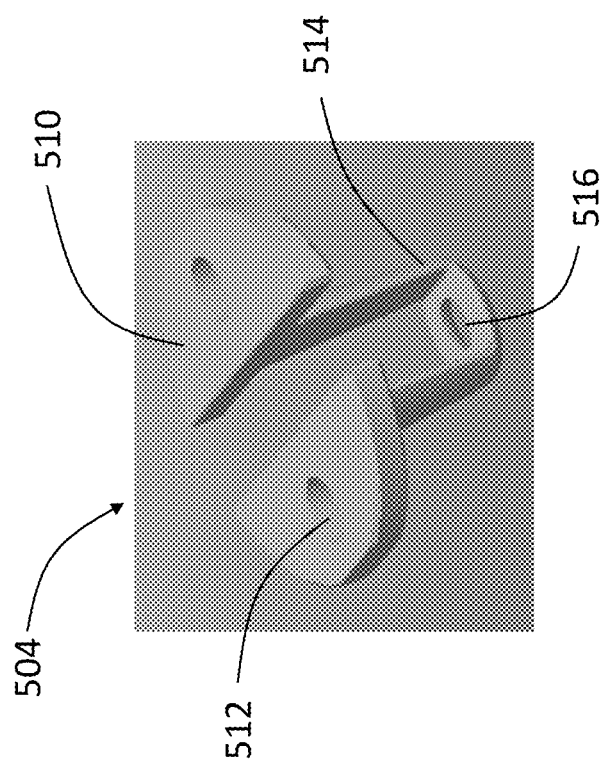
FIG. 17 is a front perspective view of a base of the humeral head trial assembly of FIG. 15.
Figure 16:
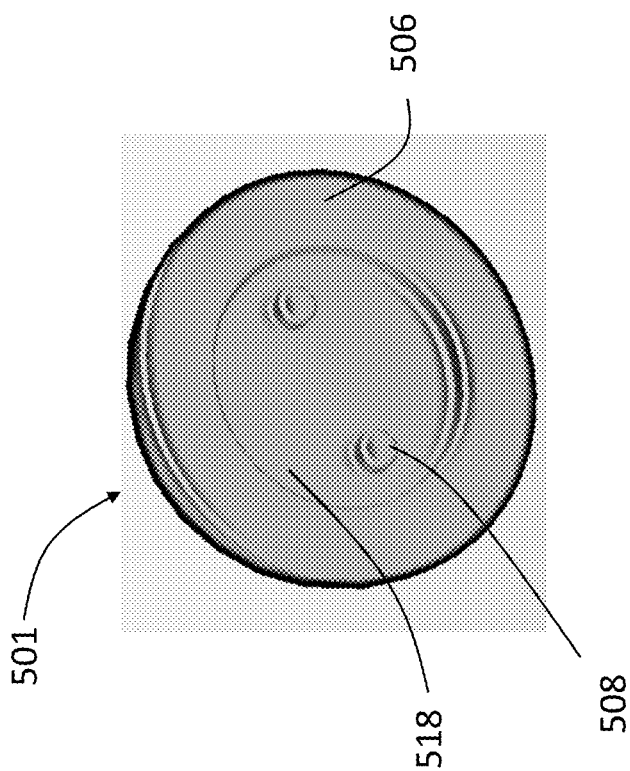
FIG. 16 is a bottom perspective view of a humeral head trial of the humeral head trial assembly of FIG. 15.

Referring now to FIGS. 15-17, there is shown a humeral head trial assembly 500 according to another embodiment of the present disclosure. Humeral head trial assembly 500 includes a humeral head trial 501 having a convex articular surface 502 and a separate base 504. Humeral head trial 501, shown isolated in FIG. 16, includes a flat surface 506 with a recessed surface 518 to receive a flat surface 510 of base 504. Recessed surface 518 may be generally circular and includes two pegs 508 which can be inserted into corresponding holes 512 on flat surfaces 510 of base 504 to secure the base to humeral head trial 501. Legs 514 of base 504 form cantilever connections with an opening 516 to allow an operator to move flat surfaces 510 by the pushing legs 514 toward each other and placing the flat surfaces in recess 518. In an exemplary use, the base 504 may first be placed into a corresponding conical/tapered hole of prosthetic humeral stem or base, for example similar to implant 10 and/or 20. The flexure of the legs 514 will tend to maintain the base 504 coupled to the prosthetic humeral stem or base via a friction fit. Then, the humeral head trial 501 may be coupled to the base 504 by passing pegs 508 into corresponding holes 512 in flat surface 510, with the flat surfaces 510 generally filling in the recess 518. Preferably, the holes 512 are oval or otherwise shaped in a complementary fashion to the pegs 508 so that there is no interference fit between the pegs 508 and the holes 512. With this configuration, after trialing is performed, the humeral head trial 501 may be removed from the base 504 simply by pulling the humeral head trial 501 off the base 504. Because there is no friction fit between the humeral head trial 501 and the base 504, there is effectively no pull-out force transmitted to the base 504 and/or the humeral implant. Then, after the humeral head trial 501 is removed, the flat surfaces 510 and legs 514 of the base 504 may be compressed and removed from the prosthetic humeral implant or base without any pull-out forces on the prosthetic humeral implant or base. It should further be noted that base 504 may be instead used with a humeral cup trial insert, generally similar to inserts 102, 202. However, such a humeral cup trial insert may instead include pins and a recess similar to that shown for humeral head trial 501 in FIG. 16.

Figure 18:
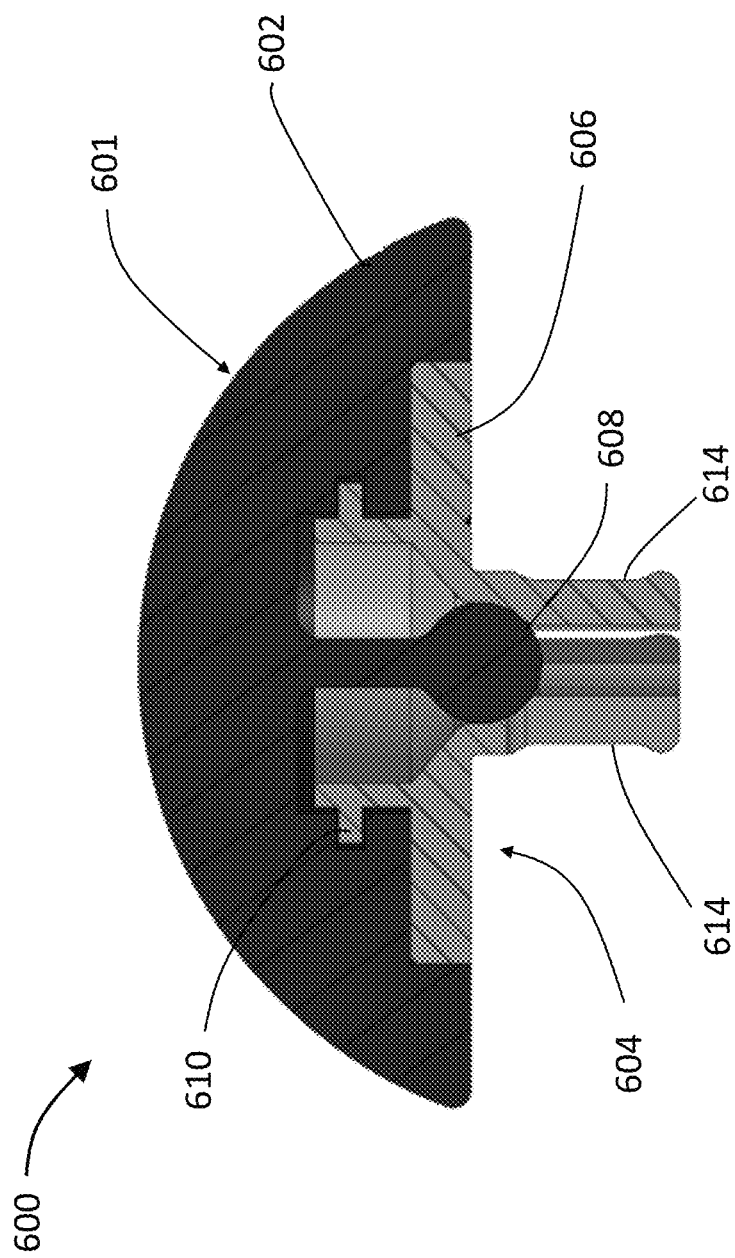
FIG. 18 is a side cross-sectional view of a humeral head trial assembly according to another embodiment of the present disclosure.
Figure 19:
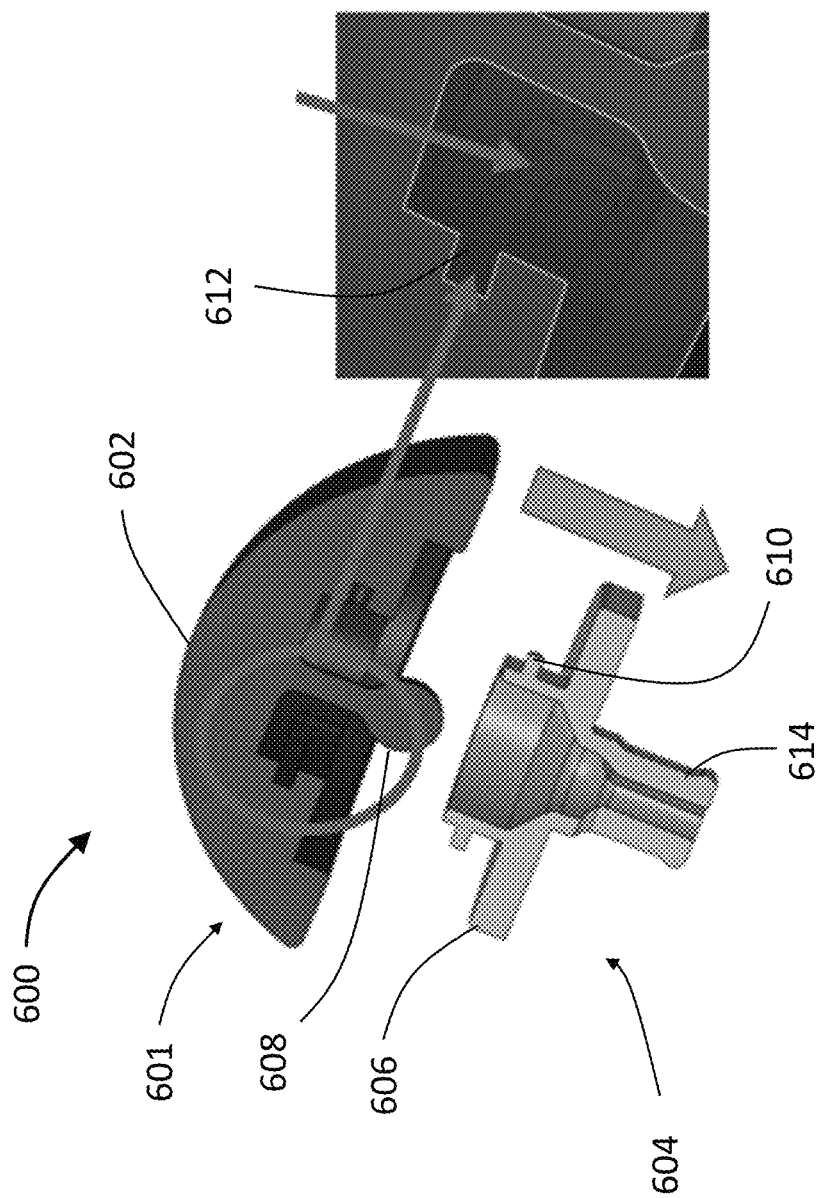
FIG. 19 is an exploded cross-sectional view of the humeral head trial assembly of FIG. 18.
Figure 20:
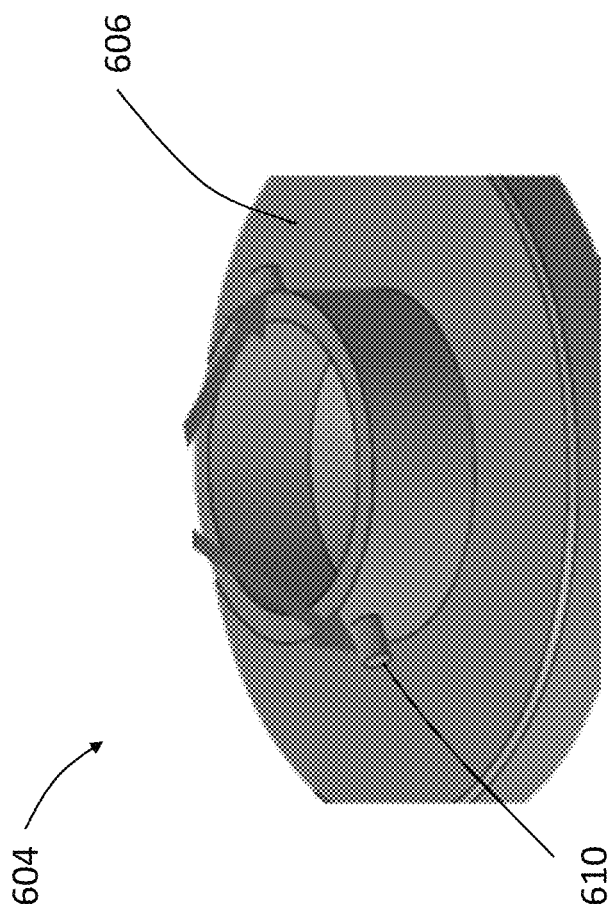
FIG. 20 is a partial view of a collet base of the humeral head trial assembly of FIG. 18.

FIGS. 18-20 show a humeral head trial assembly 600 according to another embodiment of the present disclosure. Humeral head trial assembly 600 includes a humeral head trial 601 with an articular surface 602 and a collet base 604 as best shown in the cross section of FIG. 18. A bayonet mechanism consisting of a pair of pins 610 on collet base 604 is used to secure the collet base 604 to the humeral head trial 601. Pins 610 are rotated into an L-shaped groove 612 of the humeral head trial 601 to attach and secure the collet base 604 to the humeral head trial 601 as best shown in FIGS. 18 and 19. While an L-shaped groove is shown in this embodiment, various other shaped grooves or recesses can be used in other embodiments. The collet base 604 may include a plurality of flexure legs 614 extending from a generally flat surface 606, the flexure legs in conjunction forming a generally cylindrical shape. The flexure legs 614 may have gaps between adjacent ones of the legs 614 so that the flexure legs 614 may flex radially inwardly and outwardly. The flexure legs 614 may be inserted into a corresponding conical and/or tapered (or other suitably shaped) recess in a prosthetic humeral stem or base, for example implant 10 or 20. Then the humeral head trial 601 may be inserted onto the collet base 604 so that the pins 610 slide along an axial portion of the L-shaped groove 612. As this occurs, a spherical head 608 presses against an internal tapered surface of the collet base 604 adjacent the flexure legs 614, although it should be understood that spherical head 608 may include other suitable shapes. As the spherical head 608 presses downwardly, it forces the flexure legs 614 to flex outwardly, creating a friction or interference fit between the collet base 604 and the prosthetic humeral stem or base. Then, the humeral head trial 601 may be rotated so that the pins 610 slide along the circumferential or lateral portion of the L-shaped groove 612. In this rotated position, the humeral head trial 601 is prevented from disconnection from the collet base 604, while the collet base 604 has an interference fit with the prosthetic humeral stem or base. Trialing may be performed. After trialing is complete, the humeral head trial 601 may be rotated in the opposite direction and then pulled off the collet base 604. As the spherical head 608 exits the collet base 604, the flexure legs 614 return to their contracted state allowing the collet base 604 to be removed from the prosthetic humeral stem or base without any significant pull-out force transferring to the prosthetic humeral stem or base.

Figure 22:
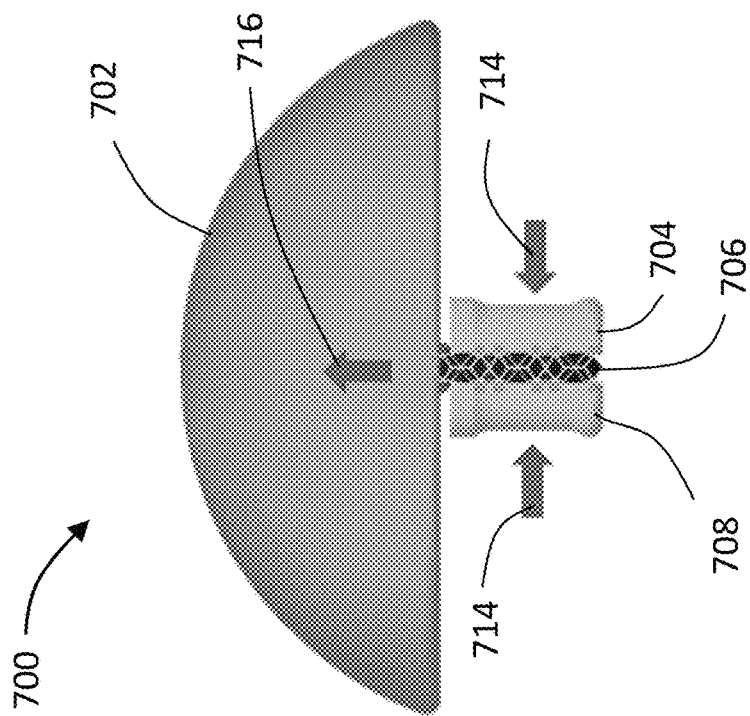
FIG. 22 is a side view of the humeral head trial of FIG. 21.
Figure 21:
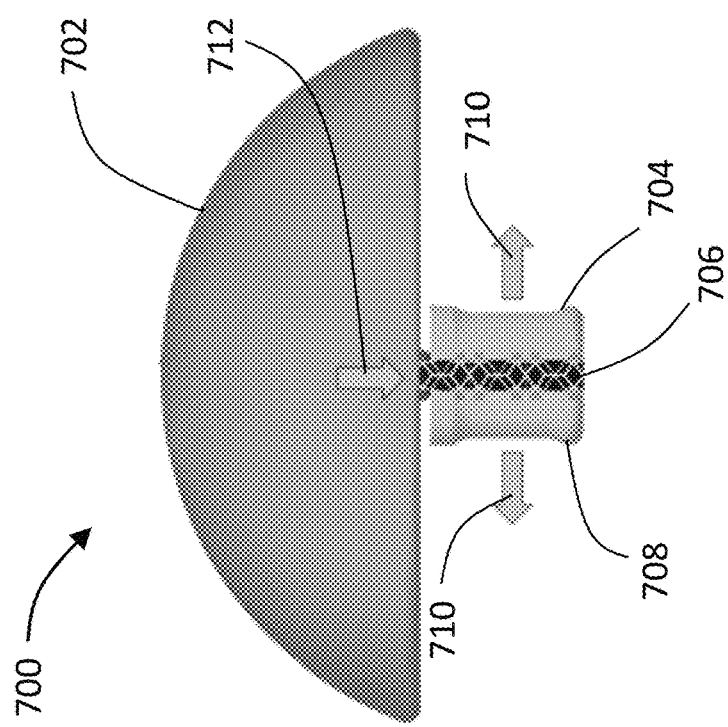
FIG. 21 is a side view of a humeral head trial according to another embodiment of the present disclosure.
Figure 23:
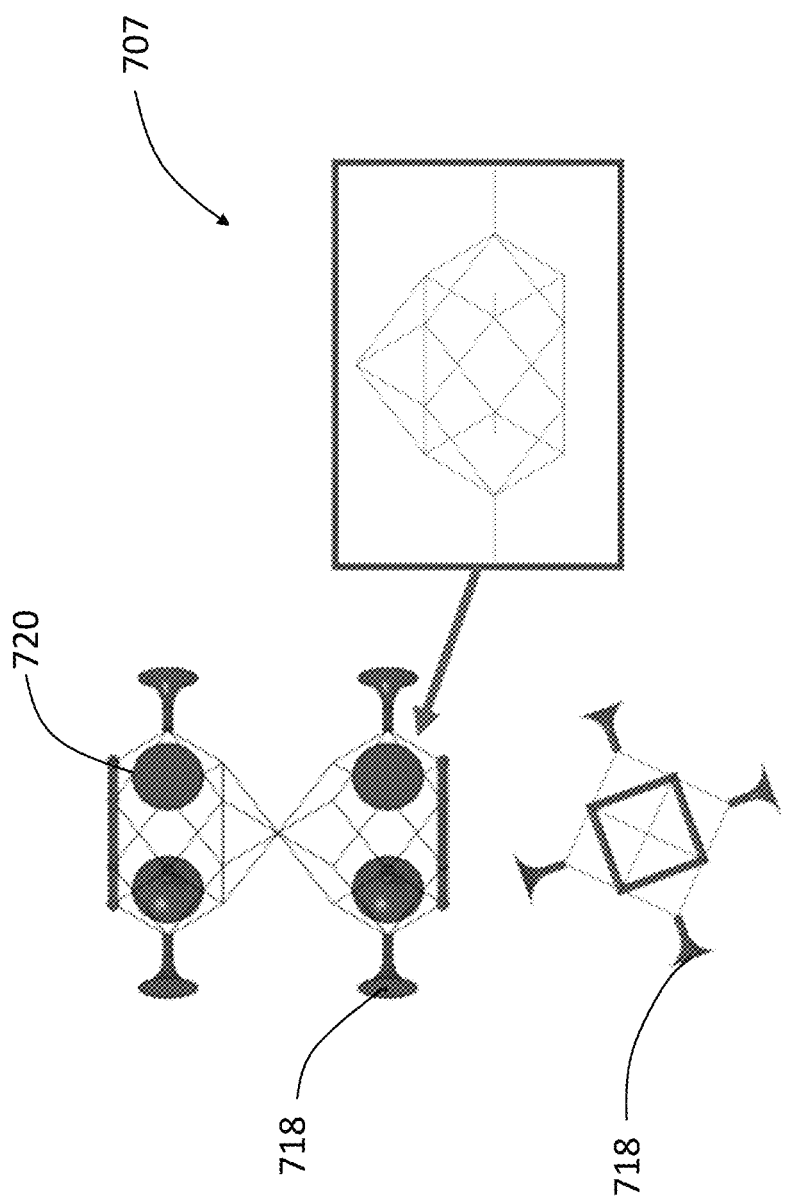
FIG. 23 is a schematic drawing of a flexure element of the humeral head trial of FIG. 21.
Figure 28:
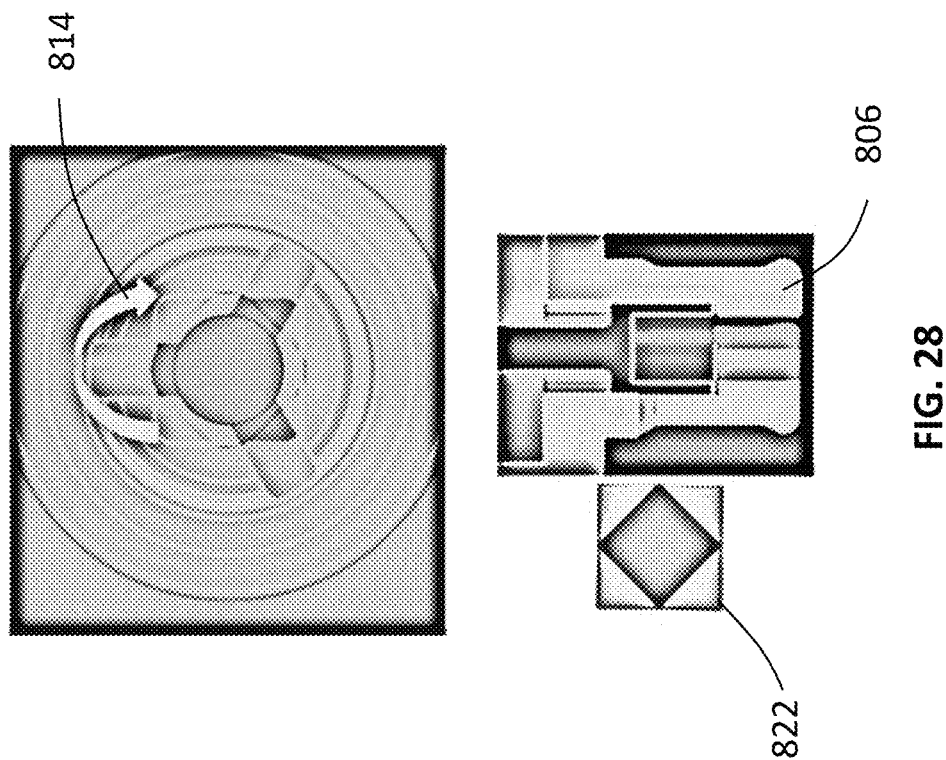
FIG. 28 is a cross-sectional view of the humeral head trial and the collet base of the humeral head trial assembly of FIG. 24 in a second locked configuration.
Figure 27:
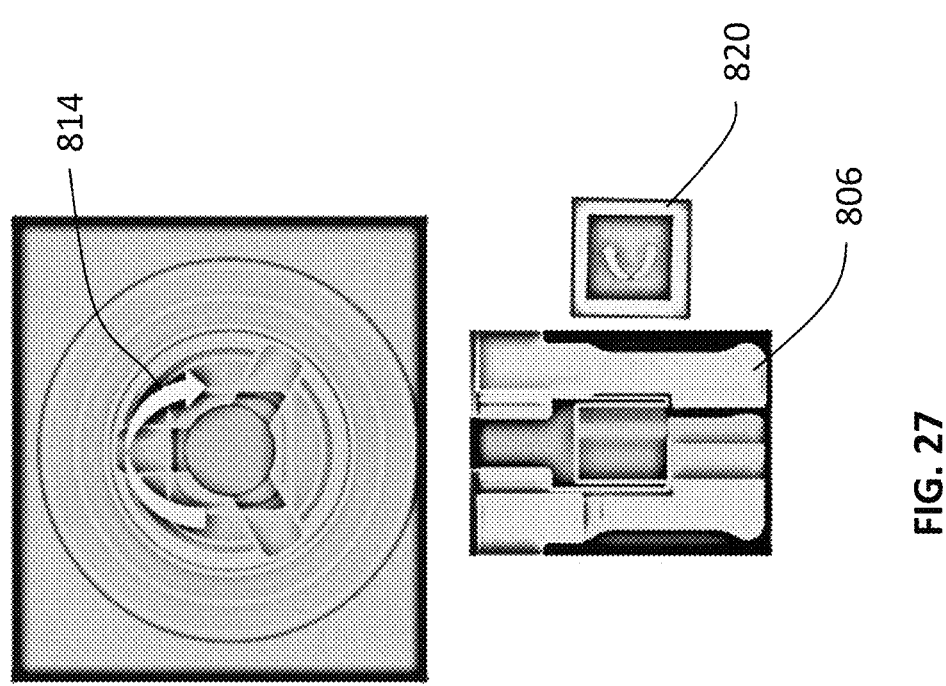
FIG. 27 is a cross-sectional view of the humeral head trial and the collet base of the humeral head trial assembly of FIG. 24 in a first unlocked configuration.
Figure 29:
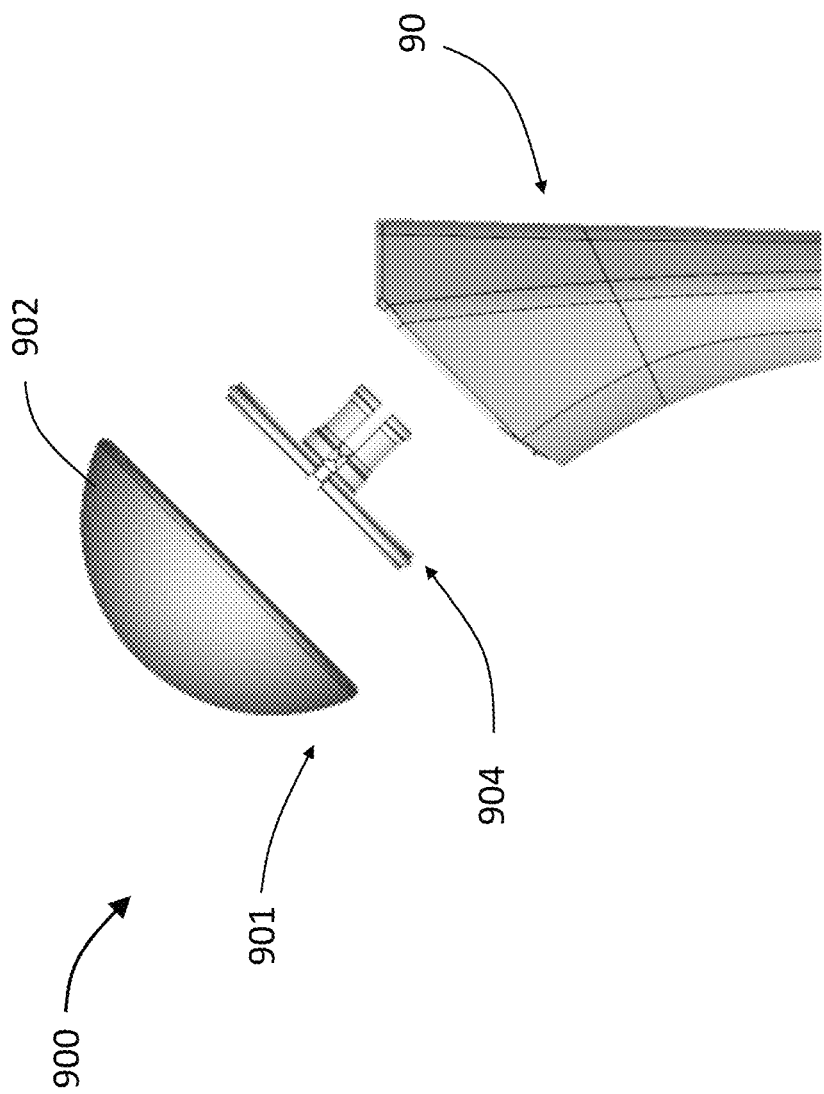
FIG. 29 is an exploded view of a humeral head trial assembly according to another embodiment of the present disclosure in conjunction with an implant.

Referring now to FIGS. 21 and 22, there is shown a humeral head trial 700 according to another embodiment of the present disclosure. Humeral head trial 700 has an articular surface 702 with a first leg 708 and a second leg 704 extending distally from a flat face of the humeral head trial 700. An elastic member 706 is positioned between the legs 704, 708 and allows first leg 708 and second leg 704 to move away from each other or be brought together depending on the force acting on the humeral head trial 700. As shown in FIG. 21, when the force is pushing down on legs 708 and 704 as indicated by direction arrow 712, legs 708 and 704 move apart as indicated by direction arrow 710. Conversely, when the applied force is pulling the humeral head trial 700 as indicated by direction arrow 716, legs 708 and 704 move closer together as indicated by direction arrows 714 as shown in FIG. 22. Thus, when humeral head trial 700 is placed in an implant, such as a conical or tapered recess of a prosthetic humeral stem or base similar to implants 10 and/or 20, force acting on the humeral head trial 700 will cause elastic member 706 to push legs 704 and 708 away from each other, and consequently secure the humeral head trial to the implant during trialing. Once trialing is completed, an operator can conveniently pull on the humeral head trial to pull out the trial without any pull-out force acting on the implant as the elastic member will now pull legs 704 and 708 toward each other and allow for easy removal of humeral head trial 700 from the implant. An example of an elastic member including a lattice structure with a single unit cell 707 is shown in FIG. 23. As shown here, interconnected struts 718 of the lattice of elastic member 706 contract radially when subject to a longitudinal force. Each strut 718 is connected to a node 720. It should be understood that a similar lattice structure could be provided with a humeral cup trial insert for use in trialing a humeral cup in an RSA procedure.

FIGS. 24-28 show a humeral head trial assembly 800 according to another embodiment of the present disclosure. Humeral head trial assembly 800 includes a humeral head trial 801 with an articular surface 802 and a collet base 804 with flexure legs 806 extending distally from the collet base. The flexure legs 806 include gaps between circumferentially adjacent legs and may together form a generally cylindrical shape, the flexure legs 806 being capable of flexing radially inwardly and outwardly. Collet base 804 includes an opening 818 at a proximal face having a rectangular profile as shown in FIG. 26, the rectangular opening 818 being positioned radially within the flexure legs 806. A corresponding generally rectangular projection 816 extending from a recessed surface 812 of humeral head trial 801 (FIG. 25) can be inserted into opening 818 and rotated along direction arrow 814 cause the flexure legs 806 to flex or splay radially outwardly FIGS. 27 and 28. In use, the flexure legs 806 of collet base 804 may first be inserted into a recess (e.g. a conical or tapered recess) of a prosthetic humeral stem or base, which may be similar to implants 10 and/or 20. The collet base 804 may easily fit into the recess while the flexure legs 806 are in a relaxed condition. Then, the humeral head trial 801 may be inserted into collet base 804. In particular, the square or rectangular projection 816 may be aligned with the square or rectangular opening 818, and the humeral head trial 801 may be pressed downwardly until the projection 816 slides into the opening 818. The collet base 804 may fit within recessed areas of the humeral head trial 801, so that the bottom surface 808 of collet base 804 may be substantially flush with a bottom surface 810 of the humeral head trial 801 when the components are assembled. After sliding the projection 816 into the opening 818, the square or rectangular faces of the projection 816 and opening 818 are aligned, as indicated by unlocked configuration 820 shown in FIG. 27. The humeral head trial 801 may then be rotated in direction 814 relative to the collet base 804 so that the corners of the rectangular projection 816 align with the flat faces of the opening 818, as indicated by locked configuration 822 in FIG. 28. In this configuration, the projection 816 forces the flexure legs 806 to splay or flex outwardly and form a friction or interference fit with the prosthetic humeral stem or base implant, locking the humeral head trial 801 in place. Trialing may be performed, and after trialing is completed, an operator can conveniently rotate humeral head trial 801 on collet base 804 in direction 814 until the projection 816 and opening 818 are again aligned in unlocked configuration 820. When the humeral head trial assembly 800 returns to this configuration, the flexure legs 806 return back to their initial position (FIG. 27), removing the friction fit between the humeral head trial assembly 800 and the prosthetic humeral stem or base implant. Then, the entire humeral head trial assembly 800 can be conveniently removed from the implant without imparting any pull-out force on the implant. It should also be understood that a similar mechanism to projection 816 may be used with a humeral cup trial insert and a similar or identical collet base 804 for trialing in an RSA procedure, as described above.

Figure 33:
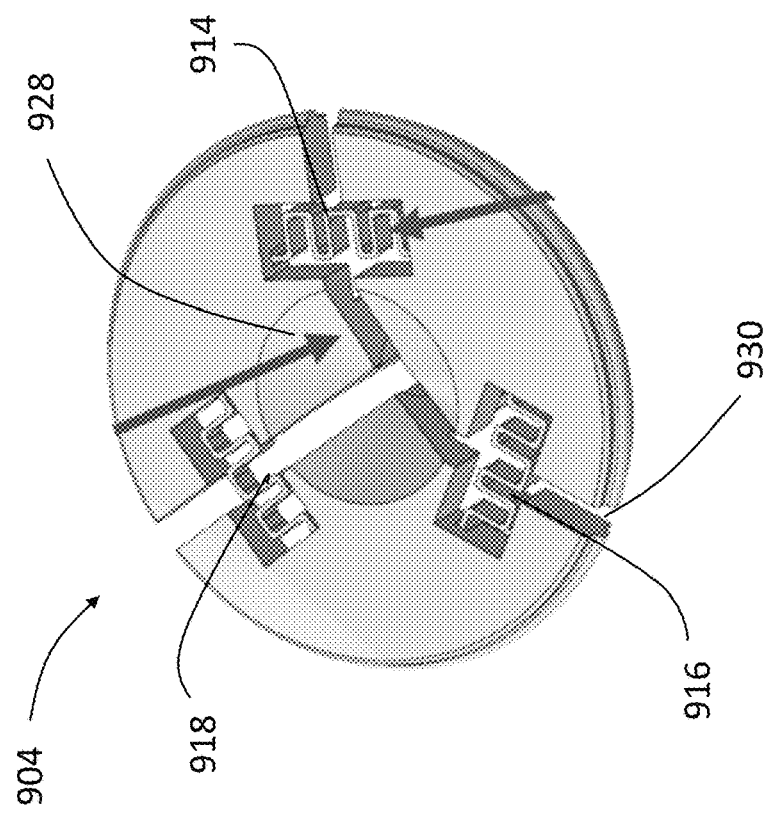
FIG. 33 is a top perspective view of a collet base of the humeral head trial assembly of FIG. 29.
Figure 32:
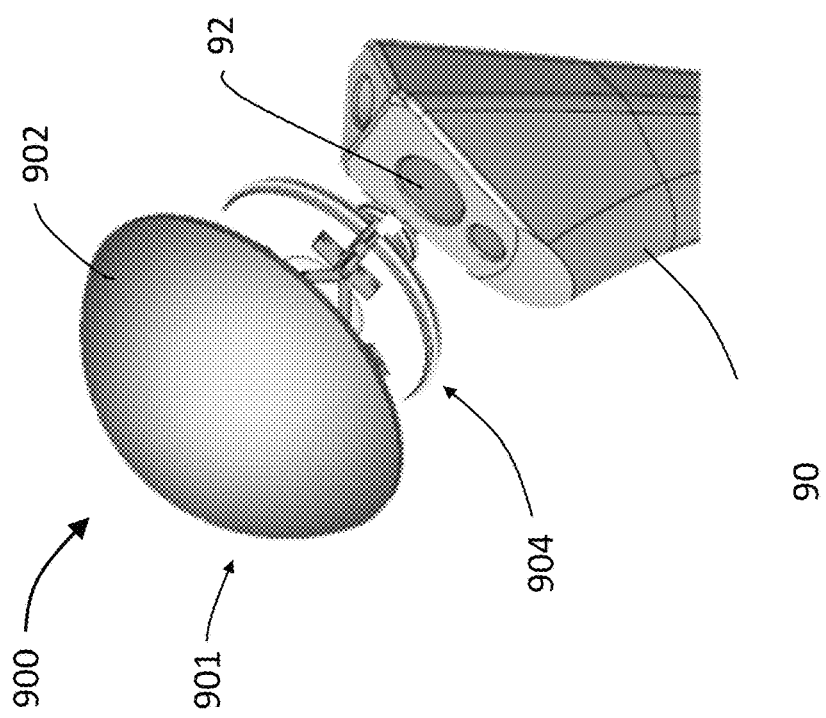
FIG. 32 is an exploded perspective view of the humeral head trial assembly of FIG. 29 in conjunction with the implant.
Figure 35:
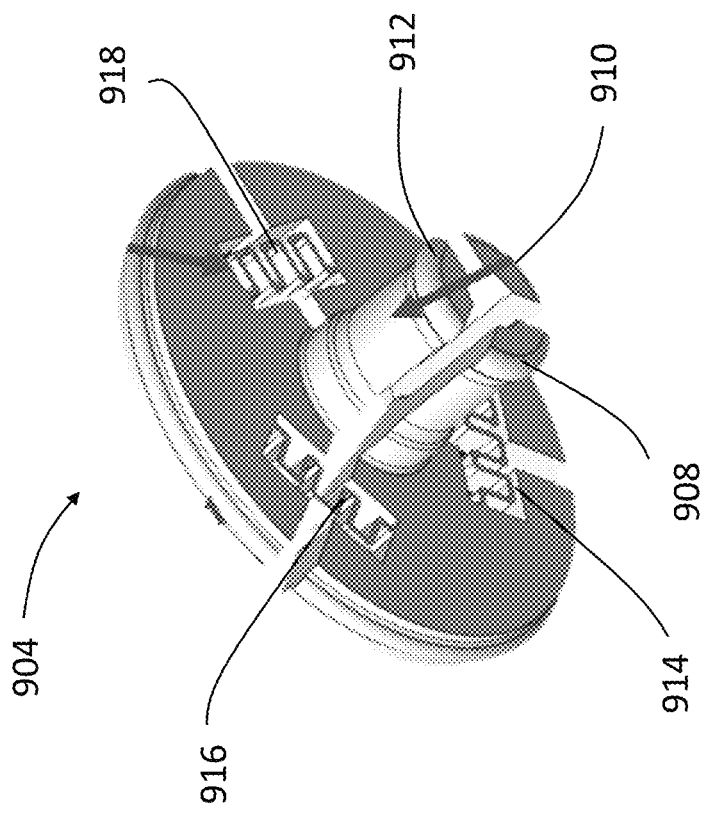
FIG. 35 is a bottom perspective view of the collet base of the humeral head trial assembly of FIG. 29.
Figure 34:
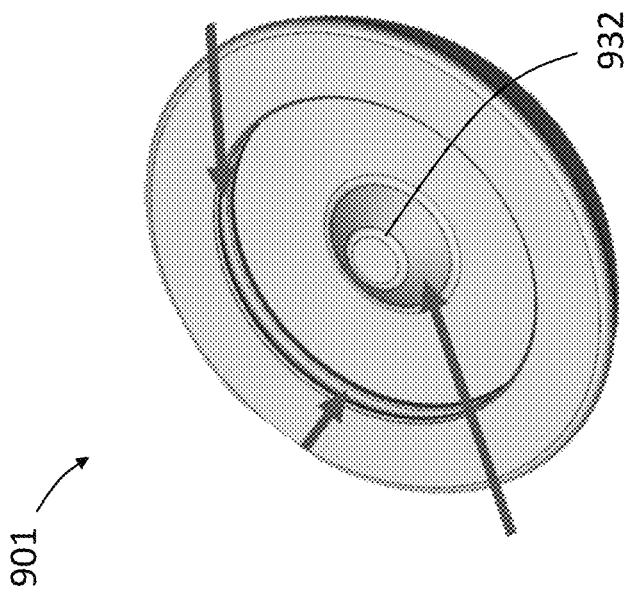
FIG. 34 is bottom perspective view of a humeral head trial of the humeral head trial assembly of FIG. 29.

Referring now to FIGS. 29-35, there is shown a humeral head trial assembly 900 according to another embodiment of the present disclosure. Humeral head trial assembly 900 is similar to humeral head trial assembly 800 and therefore like elements are referred to with similar numerals within the 900-series. For instance, humeral head trial assembly 900 includes a humeral head trial 901 having an articular surface 902 and collet base 904. However, collet base 904 includes flexure springs 914, 916, 918 as shown in FIG. 33 which allow collet base 904 to expand in order to be firmly secured to implant 90 (or any other suitable implant). Flexure springs 914, 916, 918 allow collet base 904 to expand and contract when the humeral head trial is inserted and removed from the collet base 904, respectively. A projection 932 on the flat surface of the humeral head trial (opposite the articular surface 902) may be generally conical and is configured to be placed in a complementary conical depression 928 of collet base 904 as shown in FIG. 31. When projection 932 is located in depression 928, tabs 926 on collet base 904 are pushed along direction arrow 924 to firmly secure collet base 904 to the humeral head trial, while simultaneously pushing out a first leg 908, a second leg 910, and a third leg away from each other to allow humeral head trial assembly 900 to be secured to implant 90. In the particular illustrated example, collet base 904 may include three main portions, each main portion including one of the flexure legs and a portion of the conical depression 928, with each main portion of collet base 904 coupled to the other two main portions of the collet base 904 via two of the flexure springs. A gap 930 may be provided between each adjacent pair of collet base 904 main portions. With this configuration, collet base 904 may be a single integral structure that still allows for flexing. As with other embodiments described herein, the flexure legs 908, 910, 912 may together form a generally cylindrical shape that is intended to be received within a corresponding recess 92 (e.g. a conical or tapered recess) of a prosthetic humeral stem 90 or another prosthetic humeral base. In the relaxed condition of the flexure legs 908, 910, 912, the collet base 904 may be coupled to implant 90 via recess 92 with zero or minimal friction forces. After the flexure legs 908, 910, 912 of collet base 904 are inserted into recess 92, the humeral head trial may be coupled to the collet base 904, by advancing the protrusion 932 into the corresponding depression 928 of the collet base 904. The protrusion 932 acts as a wedge to drive the three main portions of the collet base 904 away from the longitudinal center, until the tabs 926 snap into corresponding recesses within the humeral head trial. The expansion of the flexure legs in direction 922 (FIG. 31) result in an interference or friction fit between the flexure legs 908, 910, 912 and the surface of the implant 90 forming the recess 92, locking the humeral head trial assembly 900 to the implant 90. With the humeral head trial assembly 900 firmly secured to implant 90, an operator can perform trialing procedures. Upon completion of the trialing, an operator can conveniently remove humeral head trial 900 from implant 90 by first removing the humeral head trial 901 from the collet base 904. When the humeral head trial is removed from the collet base 904, the flexure springs 914, 916, 918 contract back to their initial relaxed state and pull back flexure legs 908, 910, 912 towards each other to allow for removal of the collet base 904 from implant 90 without inducing any pull-out force on the implant 90. As with other embodiments described herein, it should be understood that the features of the humeral head trial may instead be provided on a humeral cup trial insert in order to allow for trialing of a humeral cup in an RSA procedure. For example, a humeral cup trial insert similar to that described in connection with FIGS. 1-8 could be provided with a protrusion similar to protrusion 932 and used with collet base 904 in a substantially similar manner as described above.

While humeral head and cup trials in conjunction with a humeral stems are described in the embodiments above, the present disclosure can be used for any other trial such as a femoral implant trial, a tibial implant trial, etc., particularly where it is desired to minimize or eliminate pull-out force when removing the trial from another component of the system. Implant trials (and related components) of the present disclosure may be, but are not limited to, being made of any polymer such as polyetheretherketone ("PEEK"), polyarlyetherketones ("PAEK"), ultra-high molecular weight polyethylene ("UHMWPE"), metals such as titanium, stainless steel, aluminum, or other suitable material (e.g., ceramic) that is biocompatible and possess sufficient strength and rigidity. Implant trials can be made using an additive manufacturing process. The trial components can be 3d printed such that the flexible structure, posts and movable surface form a monolithic component.

Furthermore, although the invention disclosed herein has been described with reference to particular features, it is to be understood that these features are merely illustrative of the principles and applications of the present invention. It is therefore to be understood that numerous modifications, including changes in the sizes of the various features described herein, may be made to the illustrative embodiments and that other arrangements may be devised without departing from the spirit and scope of the present invention. In this regard, the present invention encompasses numerous additional features in addition to those specific features set forth in the paragraphs below. Moreover, the foregoing disclosure should be taken by way of illustration rather than by way of limitation as the present invention is defined in the examples of the numbered paragraphs, which describe features in accordance with various embodiments of the invention, set forth in the claims below.

The invention claimed is:

1. A trial kit comprising:
    a humeral trial having a first portion defining an articular surface, a second portion defining a flat surface, and a post extending from the second portion, the post having a first leg and a second leg in contact with a flexure member, the post defining a first length in a first configuration and a second length in a second configuration, the first length being greater than the second length, and
    a tool for attaching and removing the humeral trial to a humeral stem, the tool including first and second arms, wherein the first arm contacts the first leg to move the post from the first configuration to a second configuration.

2. The trial kit of claim 1, wherein the humeral trial is a humeral head trial and the articular surface is a convex articular surface.

3. The trial kit of claim 1, wherein the humeral trial is a humeral cup trial and the articular surface is a concave articular surface, the first portion being configured to be detachably coupled with the second portion.

4. The trial kit of claim 1, wherein the humeral trial is adapted to be secured to the humeral stem when the post is in an opening of the prosthetic humeral stem in the first configuration, the first length being equal to or larger than an opening length of the opening such that the post forms an interference fit with the opening in the first configuration.

5. The trial kit of claim 4, wherein the humeral trial is adapted to be detached from the humeral stem by removing the post from the opening in the second configuration, the second length being smaller than the opening length such that the post can be removed from the opening in the second configuration.

6. The trial kit of claim 5, wherein the post is adapted to be removed from the opening in the second configuration without contacting sidewalls of the opening.

7. The trial kit of claim 4, wherein the first portion is adapted to articulate with a glenoid, a glenoid implant, or a glenoid trial through a range of shoulder motion when the humeral trial is secured to the humeral stem.

8. The trial kit of claim 1, wherein the second arm contacts the second leg to move the post from the first configuration to a second configuration.

9. The trial kit of claim 1, wherein the first arm is connected to a first lever and the second arm is connected to a second lever.

10. The trial kit of claim 9, wherein the first and second arms form a hinged joint.

11. The trial kit of claim 1, wherein the first arm is received in a first groove on the second portion.

12. The trial kit of claim 11, wherein the second arm is received in a second groove on the second portion.

* * * * *